US009388130B2

(12) United States Patent
Palczewski et al.

(10) Patent No.: US 9,388,130 B2
(45) Date of Patent: *Jul. 12, 2016

(54) RETINAL DERIVATIVES AND METHODS FOR THE USE THEREOF FOR THE TREATMENT OF VISUAL DISORDERS

(75) Inventors: Krzysztof Palczewski, Bay Village, OH (US); Matthew Batten, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/619,887

(22) Filed: Sep. 14, 2012

(65) Prior Publication Data

US 2013/0072559 A1   Mar. 21, 2013

Related U.S. Application Data

(63) Continuation of application No. 13/042,308, filed on Mar. 7, 2011, now Pat. No. 9,174,936, which is a continuation of application No. 11/629,875, filed as application No. PCT/US2005/021812 on Jun. 20, 2005, now Pat. No. 7,951,841.

(60) Provisional application No. 60/580,889, filed on Jun. 18, 2004.

(51) Int. Cl.
| *C07C 403/06* | (2006.01) |
| *C07C 403/12* | (2006.01) |
| *C07C 403/14* | (2006.01) |
| *C07C 403/10* | (2006.01) |
| *C07C 403/20* | (2006.01) |
| *A61K 31/22*  | (2006.01) |
| *A61K 31/215* | (2006.01) |

(52) U.S. Cl.
CPC ............. *C07C 403/14* (2013.01); *A61K 31/215* (2013.01); *A61K 31/22* (2013.01); *C07C 403/10* (2013.01); *C07C 403/12* (2013.01); *C07C 403/20* (2013.01); *C07B 2200/09* (2013.01); *C07C 2101/10* (2013.01); *C07C 2101/16* (2013.01)

(58) Field of Classification Search
CPC .................................................... C07C 403/12
See application file for complete search history.

(56) References Cited

U.S. PATENT DOCUMENTS

| 3,196,078 A | 7/1965 | Chatzinoff et al. |
| 3,517,067 A | 6/1970 | Stern |
| 5,457,135 A | 10/1995 | Baranowitz et al. |
| 5,620,970 A | 4/1997 | Han et al. |
| 5,837,728 A | 11/1998 | Purcell |
| 5,869,468 A | 2/1999 | Freeman |
| 6,300,328 B1 | 10/2001 | Klimko |
| 6,552,009 B2 | 4/2003 | Achkar |
| 6,696,069 B2 | 2/2004 | Harichian et al. |
| 7,566,808 B2 | 7/2009 | Rando |
| 7,951,841 B2 | 5/2011 | Palczewski et al. |
| 8,324,270 B2 | 12/2012 | Maeda et al. |
| 8,962,691 B2 | 2/2015 | Palczewski et al. |
| 2002/0028849 A1 | 3/2002 | Godkin et al. |
| 2003/0215413 A1 | 11/2003 | Fares et al. |
| 2003/0228277 A1 | 12/2003 | Gehlsen |
| 2004/0022766 A1 | 2/2004 | Acland et al. |
| 2004/0097587 A1 | 5/2004 | Arbiser |
| 2004/0242704 A1 | 12/2004 | Palczewski et al. |
| 2006/0167088 A1 | 7/2006 | Widder et al. |
| 2006/0281821 A1 | 12/2006 | Palczewski |
| 2008/0221208 A1 | 9/2008 | Palczewski et al. |
| 2008/0275133 A1 | 11/2008 | Schwartz et al. |
| 2010/0035986 A1 | 2/2010 | Maeda et al. |
| 2011/0034554 A1 | 2/2011 | Washington |
| 2011/0288170 A1 | 11/2011 | Palczewski et al. |
| 2012/0041073 A1 | 2/2012 | Palczewski et al. |
| 2012/0322891 A1 | 12/2012 | Palczewski et al. |
| 2013/0072443 A1 | 3/2013 | Palczewski et al. |
| 2013/0072556 A1 | 3/2013 | Palczewski et al. |
| 2013/0072557 A1 | 3/2013 | Maeda et al. |
| 2013/0072558 A1 | 3/2013 | Maeda et al. |
| 2013/0072559 A1 | 3/2013 | Palczewski et al. |
| 2013/0072560 A1 | 3/2013 | Palczewski et al. |
| 2013/0072561 A1 | 3/2013 | Maeda et al. |
| 2013/0072568 A1 | 3/2013 | Palczewski et al. |
| 2013/0072569 A1 | 3/2013 | Palczewski et al. |
| 2013/0079403 A1 | 3/2013 | Palczewski et al. |
| 2013/0196950 A1 | 8/2013 | Palczewski et al. |

FOREIGN PATENT DOCUMENTS

| CA | 2601278 A1 | 9/2005 |
| CN | 1169854 A | 1/1998 |
| CN | 1455780 A | 11/2003 |
| CN | 198898 A | 6/2007 |
| EP | 0803248 A2 | 10/1997 |
| GB | 1449027 | 9/1976 |
| GB | 1526410 A | 9/1978 |
| JP | 61-275266 A | 5/1986 |
| JP | 6340525 A | 12/1994 |
| JP | 8198746 A | 8/1996 |
| RU | 2106843 C1 | 3/1998 |
| WO | WO 99/29315 A | 6/1995 |

(Continued)

OTHER PUBLICATIONS

Zaragoza Dorwald, Side Reactions in Organic Synthesis, 2005, Wiley-VCH Verlag GmbH & Co. KGaA, Weinheim, Preface. p. IX.*

(Continued)

*Primary Examiner* — Paul A Zucker

(74) *Attorney, Agent, or Firm* — Jacqueline F. Mahoney; Judy M. Mohr; McDermott Will & Emery LLP

(57) ABSTRACT

Compositions of and methods for using synthetic retinal derivatives as retinoid replacements and opsin agonists are provided.

12 Claims, 6 Drawing Sheets

(56) References Cited

FOREIGN PATENT DOCUMENTS

| WO | WO 96/24344 | 8/1996 |
|---|---|---|
| WO | WO 99/09969 | 3/1999 |
| WO | WO 00/68364 A2 | 11/2000 |
| WO | WO 02/055540 | 7/2002 |
| WO | WO 02/058586 A2 | 8/2002 |
| WO | WO 02/082904 A2 | 10/2002 |
| WO | WO 03/059336 A1 | 7/2003 |
| WO | WO 2004/082622 A2 | 9/2004 |
| WO | WO 2005/079774 A2 | 9/2005 |
| WO | WO 2006/002097 A2 | 1/2006 |
| WO | WO 2006/033734 A2 | 3/2006 |

OTHER PUBLICATIONS

Howard et al, Archives of Toxicology, Comparative Distribution, Pharmacokinetics and Placental Permeabilities of All-trans-Retinoic Acid, All-trans-4-oxo-Retinyl Acetate and 9-cis-Retinal in Hamsters, 1989, 63, pp. 112-120.*

Maugard et al, Biotechnology Progress, Synthesis of Water-Soluble Retinol Derivatives by Enzymatic Method, 2002, 18, pp. 424-428.*

Huttunen et al., "Prodrugs—from Serendipity to Rational Design", Pharmacologica Reviews, vol. 63, No. 3, pp. 750-771 (2011).

Newton et al., "Structure-Activity Relationships of Retinoids in Hamster Tracheal Organ Culture", Cancer Res., vol. 40, pp. 3413-3425 (1980).

Perusek and Maeda, "Vitamin A Derivatives as Treatment Options for Retinal Degenerative Disease", Nutrients, vol. 5, pp. 2646-2666 (2013).

Ohgane et al., "Retinobenzaldehydes as proper-trafficking inducers of folding-defective p23H rhodopsin mutant responsible for retinitis pigmentosa", Bioorg. Med. Chem., vol. 18, No. 19, pp. 7022-7028 (2010).

Ablonczy et al., "11-cis-retinyl reduces constitutive phosphorylyzation and improves quantum catch in retinoid-deficient mouse rod photoreceptors", J. Biol. Chem., vol. 227, pp. 40491-40498 (2002).

Acland et al., "Gene therapy restores vision in a canine model of childhood blindness", Nature Genetics, vol. 28, pp. 92-95 (2001).

Acland et al., "Long-term restoration of rod and cone vision by single dose rAAV-mediated gene transfer to the retinain a canine model of childhood blindness", Mol. Ther., vol. 12, No. 6, pp. 1072-1082 (2005).

Aggarwal et al., "2-Halogeno-1,3-dithiane 1,3-dioxide: a diastereoselective carbonyl anion equivalent in reactions with aldehydes", J. Chem. Soc., vol. 1, pp. 11-19 (1997).

Albeck et al., "Factors Affecting the Absorption Maxima of Acidic Forms of Bacteriorhodopsin", Biophys. J., vol. 56, pp. 1259-1265 (1989).

Aleman et al., "Impairment of the transient papillary light reflex in Rpe65(-/-) mice and humans with leber congenital amaurosis", Invest. Opthalmol. Vis. Sci., vol. 45, No. 4, pp. 1259-1271 (2004).

Asato et al., "Flourinated rhodopsin analogues from 10-flouro- and 14-flouroretinal", J. Am. Chem. Soc., vol. 100, No. 18, pp. 5957-5960 (1978).

Baehr et al., "The retinold cycle and retina disease", Vision Research, vol. 43, pp. 2957-2958 (2003).

Batten et al., "Lecithin-retinol acyltransferase is essential for accumulation of all-trans-retinyl ester in the eye and in the liver" The Journal of Biological Chemistry, vol. 279, No. 11, pp. 10422-10432 (2004).

Batten et al., "Pharmacological and rAAV gene therapy rescue of visual functions in a blind mouse model of leber congenital amaurosis", PLoS Medicine, vol. 2, Issue. 11, No. e333, pp. 1177-1189 (2005).

Beischel et al., "Azidotetrafluorophenyl retinal analogue: synthesis and bacteriorhodopsin pigment formation", Photochemistry and Photobiology, vol. 60, No. 1, pp. 64-68 (1994).

Bernstein et al., "Biochemical characterization of the retinoid isomerasa system of the eye", J. Biol. Chem., vol. 262, No. 35, pp. 16848-16857 (1987).

Berson et al., "A randomized trial of vitamin A and vitamin E supplementation for retinitis Piamentosa", Arch. Opthamot, vol. 111, pp. 761-772 (1993).

Berson et al., "Retinitis pigmentosa: unfolding its mystery", Proc. Natl. Sci. USA, vol. 93, pp. 4526-4528 (1996).

Berson, "Treatment of retinitis Pigmentosa with vitamin A", Digital J. Opthamol., vol. 4, No. 7 Massachusetts Eye and Ear Infirmary, Harvard Medical School (1998).

Berson et al., "Disease progression in patients with dominant retinitis pigmentosa and rhodopsin mutations" Invest. Opthalmol. Vis. Sci., vol. 43, No. 9, pp. 3027-3036 (2002).

Biesalski et al, "Sensitive Analysis of Retinyl Esters by Isocratic Adsorption Chromatography", J. Clin. Chem. Clin. Biochem., vol. 27, No. 2, pp. 65-74 (1989) Abstract only.

Birnbach et al., "Retinoic acid accelerates photoreceptor cell death by apoptosis in Pro23HIS rhodopsin transgenic mice", Invest. Opthalmol. Vis. Sci., vol. 38, No. 4, pp. s311 (1997).

Boehm et al., "Photoaffinity labeling studies of bacteriorhodopsin with [15-$^{3}$h]-3-Diazo-4-keto-all-trans-retinal". J. Am. Chem. Soc., vol. 112, pp. 7779-7782 (1990).

Borhan et al, "Chemoenzymatic synthesis 1-cis-retinal photoaffinity analog by use of squid retinochrome", J. Am. Chem. Soc., vol. 119, pp. 5758-5759 (1997).

Borhan et al., "Efficient synthesis of 11-cis-retinoids", Chem. Eur. J., vol. 5, No. 4, pp. 1172-1175 (1999).

Bridges, "Vitamin A* and the Role of the Pigment Epithelimn during Bleaching an Regeneration of Rhodopsin in the Frog Eye", Exp. Eye Res., vol. 22, pp. 435-455 (1976).

Buczylko et al., "Mechanisms of opsin activation", J. Biol. Chem., vol. 271, No. 34, pp. 20621-20630 (1996).

Caldwell et al, "Synthesis of retinals with eight- and nine-membered rings in the side chain models for rhodopsin photobleaching intermediates", J. Org. Chem., vol. 58, pp. 3533-3537 (1993).

Capecchi, "Altering the genome by homologous recombination", Science, vol. 224, No. 4910, pp. 1288-1292 (1989).

Carney and Russell, "Correlation of Dark Adaptation Test Results with Serum Vitamin A Levels in Diseased Adults", J. Nutr., vol. 110. pp. 552-557 (1980).

Caruso et al, "Effects of fenretinide (4-HPR) on dark adaptation", XP002475887; STN Database Accession No. 1998:418096 & Archives of Opthalmology (Chicago), vol. 116, No. 6, pp. 759-763, CODEN: AROPAW; ISSN:0003-9950, (1998) Abstract only.

Chapple et al., "Looking at protein misfolding neurodegenerative disease through retinitis piamentosa", ACNR, vol. 3, Issue 1, pp. 12-13 (2003).

Chatzinoff et al., "Eleven-cis vitamin A in the treatment of retinitis Pigmentosa", Arch. Opthalmol., vol. 80, pp. 417-419 (1968).

Cideciyan et al., "Rod and cone visual cycle consequences of a null mutation in the 11-cis-retinol dehydrogenase gene in man", Vis. Neurosci., vol. 17, No. 5, pp. 667-678 (2000).

Colmenares et al., "11,12-Difluororhodopsin and related odd-numbered fluororhodopsins. the use of $J_{F,F}$ for following a cis-trans isomerization process", J. Am. Chem. Soc., vol. 121, pp. 5803-5804 (1999).

Congdon et al., "Responsiveness of dark-adaptation threshold to vitamin A and β-carotene supplementation in pregnant and lactating women in Nepal", Am. J. Clin. Nutr., vol. 72, pp. 1004-1009 (2000).

Corson et al., "Sensitization of bleach rod photoreceptors by 11-cis-locked analogues of retinal", PNAS USA, vol. 87, pp. 6823-6827 (1990).

Crescitelli and Pearlman, "Can isorhodopsin be produced in the living rat?", Vision Res., vol. 13, pp. 2515-2525 (1973).

Crescitelli et al., "The spectral properties and photosensitivies of analogue photopigments regenerated with 10- and 14-substituted retinal analogues" Proc. R. Soc. Lond. B, vol. 233, pp. 55-76 (1988).

Crouch et al., "Photo sensitive pigments formed with rat opsin", Investigative Opthalmology, vol. 15, No. 10, pp. 872-875 (1976).

Crouch and Katz, "The effect of retinal isomers on the ver and erg of vitamin A deprived rats", Vision Res., vol. 31, pp. 109-115 (1980).

Crouch et al., "Inhibition of rhodopsin regeneration of cyclohexyl derivatives", Vision Research, vol. 22, No. 12, pp. 1451-1456 (1982).

Crouch et al., "Opsin pigments formed with acyclic retinal analogues", FEBS, vol. 158, No. 1, pp. 139-142 (1983).

(56) References Cited

OTHER PUBLICATIONS

Crouch et al., "Cycloheptatrienylidene analog of 11-cis retinal", Invest. Opthamol. Vis. Sci., vol. 25, pp. 419-418 (1984).
Crouch et al., "Yearly review: studies of rhodopsin and bacteriorhodopsin using modified retinals", Photochemistry and Photobiology, vol. 44, No. 6, pp. 803-807 (1986).
De Grip et al., "10 20 methanorhodopsins 7e 9e 13e-10 20 mthanorhodopsin and 7e 9z 13z-10 20 methanorhodopsin 11-cis-locked rhodopsin analog pigments with unusual thermal and photostability", Eur. J. Biochem., vol. 191, No. 1. pp. 211-220 (1990).
Delange et al., "An additional methyl group at the 10-position of retinal dramatically slows down the kinetics of the rhodopsin photocascade", Biochemistry, vol. 37, No. 5, pp. 1411-1420 (1998).
Drachev et al., "An investigation of the electrochemical cycle of bacteriorhodopsin analogs with the modified ring", Arch. Biochem. Biophys., vol. 270, No. 1, pp. 184-197 (1989).
Driessen et al., "Disruption of the 11-cis-retinol dehydrogenase gene leads to accumulation of cis-retinols and cis-retinyl esters", Mol. Cell Biol., vol. 20, No. 12, pp. 4275-4287 (2000).
Ebrey et al., "Properties of several sterically modified retinal analogs and their photosensitive pigments", Biochemistry, vol. 14, No. 18, pp. 3933-3941 (1975).
European Search Report From related European Patent Applicaion No. EP 04757476, mailed on Jun. 5, 2008.
European Search Report From Related European Patent Application No. EP 1154402, search completed on Sep. 5, 2011.
European Search Report From Related European Patent Application No. EP 1154404, search completed on Sep. 6, 2011.
European Search Report From Related European Patent Application No. EP 1154534, search completed on Sep. 5, 2011.
Eyring el al., "Assignment and interpretation of hydrogen out-of-plane vibrations in the resonance raman spectra of rhodopsin and bathorhodopsin", Biochemistry, vol. 21, pp. 384-393 (1982).
Fan et al., "Isorhodopsin rather than rhodopsin mediates rod function RPE65 knock-out mice" PNAS, vol. 100, No. 23, pp. 13662-13667 (2003).
Fujimoto et al., "On the bioactive conformation of the rhodopsin chromophore: absolute sense of twist around the 6-s-cis bond", Chem. Eur. J., vol. 7, No. 19, pp. 4198-4204 (2001).
Fujimoto et al., "Solution and biologicaily relevant conformations of enantiomeric 11-cis-locked cyclopropyl retrials", J. Am. Chem. Soc., vol. 124, pp. 7294-7302 (2002).
Fukada et al., "Studies on structure and function of rhodopsin by use of cyclopentatrienylidene 11-cis-locked rhodopsin", Biochemistry, vol. 23, No. 24, pp. 5826-5832 (1984).
Futterman et al., "The composition of liver vitamin A ester and the synthesis of vitamin A ester by liver microsomes", J. Biol. Chem., vol. 239, No. 12, pp. 4077-4080 (1964).
Gao and Hollyfield, "Aging of the human retina" Inv. Opth. Vis. Sci., vol. 33, pp. 1-17 (1992).
Gartner et al,, "Quantum yield of chapso-solubilized rhodopsin and 3-hydroxy retinal containing bovine opsin", Photochemistry and Photobiology, vol. 54, No. 6, pp. 1047-1055 (1991).
Geroski et al., "Drug delivery for posterior segment eye disease", IOVS, vol. 41, No. 5, pp. 961-964 (2000).
Grant et al., "Treatable forms of retinitis pigmentosa associated with systemic neurological disorders", Int. Opthalmol. Clin., vol. 41, No. 1, (2001) printed from http://www.ncbi.nim.nih.gov/pubmed/11198137 on Jan. 14, 2009 Abstract only.
Haeseleer et al., "Dual-substrate specificity short chain retinol dehydrogenases from the vertebrate retina", J. Biol. Chem., vol. 277, No. 47, pp. 45537-45546 (2002).
Haig et al., "Vitamin A and Rod-Cone Dark Adaption in Cirrhoses of the Liver", Science, vol. 87, No. 2267, pp. 534-536 (1938).
Han et al., "The C9 methyl group of retinal interacts with glycine-121 in rhodopsin", PNAS, vol. 94, pp. 13442-13447 (1997).

Harvard Health Publications, "The aging eye: preventing and treating eye disease", Harvard Helath Publications, 3 pgs. (2011) printed from http://www.health.harvard.edu/special_health_reports/the_Aging_Eye on Nov. 5, 2011.
Head, "Natural therapies for ocular disorders, part one: diseases of the retina", Alt. Med. Review, vol. 4, No. 5, pp. 342-359 (1999).
Hiraki et al., "Bacteriorhodopsin analog regenerated with 13-desmethyl-13-lodoretinal", Biophysical Journal, vol. 83, pp. 3460-3469 (2002).
Hirano et al., "Constraints of opsin structure on the ligand-binding site: studies with ring-fused retinals", Photochemistry and Photobiology, vol. 76, No. 6, pp. 606-615 (2002).
Hisatomi et al., "Critical role of photoreceptor apoptosis in functional damage after retinal detachment", Curr. Eye Res., vol. 24, No. 3, 161-172 (2002) Abstract only, 1 pg., printed from http://www.ncbi,nim.nih.gov/pubmed/12221523.
Hu et al., "Unbleachable rhodopsin with an 11-cis-locked eight-membered ring retinal: the visual transduction process", Biochemistry, vol. 33, pp. 408-416 (1994).
Illing et al., "A Rhodopsin mutant linked to autosomal dominant retinitis pigmentosa is prone to aggregate and interacts with ubiquitin proteasome system", J. Biol. Chem., vol. 277, No. 37, pp. 34150-34160 (2002).
Imai et al., "Probing for the threshold energy for visual transduction: red-shifted visual pigment analogs from 3-methoxy-3-dehydroretinal and related compounds", Photochemistry and Photobiology, vol. 70, No. 1, pp. 111-115 (1999).
Imamoto et al., "Structure around $C_6$—$C_7$ bond of the chromophore in bathorhodopsin: low-temperature spectroscopy of 6s-cis-locked bicyclic rhodopsin analogs", Biochemistry, vol. 35, pp. 6257-6262 (1996).
Imanishi et al., "Noninvasive two-photon imaging reveals retinyl ester storage structures in the eye", Cell Biol. vol. 164, pp. 373-383 (2004).
International Search Report from related PCT Patent Application No. PCT/US2004/007987 mailed on Dec. 3, 2004, application now published as International Publication No. WO2004/082622, published on Sep. 30, 2004.
International Search Report from related PCT Patent Application No. PCT/US2005/021812 mailed on Dec. 28, 2005, application now published as International Publication No. WO2006/002097, published on Jan. 5, 2006.
International Search Report from related PCT Patent Application No. PCT/US2009/000824 mailed on Nov. 5, 2009, application now published as international Publication No. WO2009/102418, published on Aug. 20, 2009.
Jackson et al., "Aging and scotopic sensitivity", Vis. Res., vol. 38, pp. 3655-3662 (1998).
Jackson et al., "Aging and dark adaption", Vis. Res. vol. 39, pp. 3675-3982 (1999).
Jackson et al., "Photoreceptor degeneration and dysfunction in aging and age-related maculopathy", Aging Res. Rev., vol. 1, No. 3, pp. 381-396 (2002).
Jacobson et al., "Retinal degenerations with truncation mutations in the cone-rod homeobox (CRX) gene", Invest. Opthalmol. Vis. Sci., vol. 39, No. 12, pp. 2417-2426 (1988).
Jacobson et al., "Night blindness in Sorsby's fundus dystrophy reversed by vitamin A" Nat. Genet. vol. 11, pp. 27-32 (1995).
Jacobson et al., "Phenotypic Marker for Early Disease Detection in Dominant Late-Onset Retinal Degeneration", IOVS, vol. 42, No. 8, pp. 1882-1890 (2001).
Jacobson et al., "Identifying photoreceptors in blind eyes caused by RPE65 mutations: Prerequisite for human gene therapy success", PNAS USA, vol. 102, No. 17, pp. 6177-6182 (2005).
Jang, "Mechanism of rhodopsin activation as examined with ring-constrained retinal analogs and the crystal structure of the ground state protein", The Journal of Biological Chemistry, vol. 276, No. 26148-26153 (2001).
Jang et al., "Characterization of a dehydrogenase activity responsible for oxidation of 11-cis-retinol in the retinal pigment epithelium of mice with a disrupted RDH5 gene. A model for the human heredity disease fundus albunctatus", J. Biol. Chem., vol. 276, No. 35, pp. 32456-32465 (2001).

(56) References Cited

OTHER PUBLICATIONS

Jin et al., "Noncovalent occupancy of the retinal-binding pocket of opsin diminishes bleaching adaption of retinal cones", Neuron, No. 11, pp. 513-522 (1993).
Karnaukhova et al., "Bioactivity of visual pigments with sterically modified retinal analogs", Bioorganic Chemistry, vol. 27, pp. 372-382 (1999).
Kefalov et al., "Role of noncovalent binding of 11-cis-retinal to opsin in dark adaption of rod and cone photoreceptors", Neuron, vol. 29, Issue 3, pp. 749-755 (2001).
Kemp et al,, "Visual Function and Rhodopsin Levels in Humans with Vitamin A Deficiency", Exp. Eye Res., vol. 46, pp. 185-197 (1988).
Kirillova et al., "Cyclopentene and cyclohexene retinal analogs react differenly with bacterioopsin", Chemical Abstracts, vol. 120, pp. 557 (1994) Abstract No. 128:187138 Abstract only.
Kubo et al, "Effect of vitamin A palmitate on vitamin A-deficient rabbits", XP002475885; STN Database Accession No. 2000:172779 & Nippon Ganka Gakkai Zasshi, vol. 103, No. 10, pp. 729-733 CODEN:NGZAA6; ISSN: 0029-0203, 1999 Abstract only.
Kuksa et al., "Biochemical and physiological properties of rhodopsin regenerated with 11-cis-6-ring- and 7-ring-retinals", The Journal of Biological Chemistry, vol. 277, No. 44, pp. 42315-42324 (2002).
Kuksa et al., "Retinoid cycle in the vertebrate retina: experimental approaches and mechanisms of isomerization", Vision Research, vol. 43, pp. 2959-2981 (2003).
Kupfer et al., "Information for doctors who follow patients with retinitis pigmentosa", National Eye Institute (1993), printed from http://www.nei.nih.gov/news/clinicalalerts/alert-rp.asp on Jan. 15, 2009, 2 pages.
Lamb and Pugh, "Dark adaption and the retinoid cycle of vision", Prog. Retin. Eye Res., vol. 23, pp. 307-380 (2004).
Lamb and Pugh, "Phototransduction, Dark Adaptation, and Rhodopsin Regeneration", IOVS, vol. 47, No. 12, pp. 5138-5152 (2006).
Lang, "Ocular drug delivery conventional ocular formations", Adv. Drug Del. Rev., vol. 16, No. 1, pp. 39-43 (1995).
Lawson et al., "Retinal analog restoration of photophobic responses in a blind chlamydomonas-reinhardtll mutant evidence for an archaebacterial like chromophore in a eukaryotic rhodopsin", Biophysical Journal, vol. 60, No. 6, pp. 1490-1498 (1991).
Lewin et al., "Synthesis and characterization of trans-, 13-cis-, and 11-cis, 13-cis-12-(hydroxymethyl)retinols", J. Org. Chem., vol. 49, pp. 649-652 (1984).
Lewis et al., "Steric barrier to bathorhodopsin decay in 5-demethyl and mesityl analogs of rhodopsin", J. Am. Chem. Soc., vol. 123, pp. 10024-10029 (2001).
Li et al., "Effect of vitamin A supplementation of rhodopsin mutants threonine-17→methionine and proline-347→serine in transgenic mice and in cell cultures", Proc. Natl. Acad. Sci. USA, vol. 95, pp. 11933-11938 (1998).
Li et al., "Delivery of 9-cis retinal to photoreceptors from bovine serum albumin", Photochem. Photobiol., vol. 69, No. 4, pp. 500-504 (1999).
Lin et al., "Vibrational Assignment of Torsional Normal Modes of Rhodopsin: Probing Excited-State Isomerization Dynamics along the Reaction $C_{11}$—$C_{12}$ Torsion Coordinate", J. Phys. Chem. B, vol. 102, pp. 2787-2806 (1998).
Liu et al., "The nature of restriction in the binding site of rhodopsin. A model study", J. Am. Chem. Soc., vol. 106, No. 26. pp. 8298-8300 (1984).
Maeda et al., "Evaluation of the role of the retinal g protein-coupled receptor (RGR) in the vertebrate retina in vivo", Journal of Neurochemistry, vol. 85, pp. 944-956 (2003).
Maeda et al., "Improvement in Rod and Cone Function in Mouse Model of *Fundus albipunctatus* after Pharmacologic Treatment with 9-*cis*-Retinal", IOVS, vol. 47, No. 10, pp. 4540-4546 (2006).
Maeda et al., "Effects of long-term administration of 9-cis-retinyl acetate on visual function in mice", Inv. Opth. Vis. Sci., vol. 50, No. 1, pp. 322-332 (2009).
Massoud et al., "Plasma vitamin A and beta-carotene in retinitis pigmentosa", Brit. J. Opthal., vol. 59, pp. 200-204 (1975).
Mata et al., "Substrate specificity of retinyl ester hydrolase activity in retinal pigment epithelium", Journal of Lipid Research, vol. 39, pp. 604-612 (1998).
Matsukawa et al., "Role of purpurin as a retinal-binding protein in goldfish retina during the early stage of optic nerve regeneration: Its priming action on neurite outgrowth", J. Neurosci., vol. 24, No. 38, pp. 8346-8353 (2004).
Maugard et al., "Enzymatic synthesis of derivatives of vitamin A in organic media", J. Mol. Cat. B, vol. 8, pp. 275-280 (2000).
Maxwell et al., "Photodynamic responses in rhodotorula glutinis in the absence of added sensitizers", Photochemistry and Photobiology, vol. 13, No. 3, pp. 259-273 (1971).
Mayo Clinic, "Retinal detachment", 8 pgs. (2010) printed from http://www.mayoclinic.com/health/retinal-detachment/DS00254/METHOD=print&DSECTION=all.
McBee et al., "Isomerization of 11-cis-retinoids to all-trans-retinoids in vitro and in vivo", J. Biol. Chem., vol. 276, No. 51, pp. 48483-48493 (2001).
McBee et al. "Confronting complexity: the interlink of phototransduction and retinoid metabolism in the vertebrate retina", Prog. Ret. Eye Res., vol. 20, No. 4, pp. 469-529 (2001).
MedlinePius, "Diabetic retinopathy", 5 pgs. (2011) printed from http://www.nim.nih.gov/medlineplus/ency/article/00212.htm.
Mizukami et al., "Photoisomerization mechanism of the rhodopsin chromophore: picosecond photolysis of pigment containing 11-cis-locked eight-membered ring retinal", PNAS, vol. 90, pp. 4072-4076 (1993).
Nakamura et al., "A high association with cone dystrophy in fundus albipunctatus caused by mutations of the RDH5 gene", Invest. Opthalmol. Vis. Sci., vol. 41, No. 12, pp. 3925-3932 (2000).
Nishiguchi et al., "A novel mutation (I143NT) in guanylate cyclase-activating protein 1(GCAP1) associated with autosomal dominant cone degeneration", Invest. Opthalmol. Vis. Sci., vol. 45, No. 11, pp. 3863-3870 (2004).
Nöll, "Suitability of retinol, retinal and retinyl palmitate for the regeneration of bleached rhodopsin in the isolated frog retina", XP002486105, STN Database Accession No. 1985:164043 & Vision Research. vol. 24, No. 11, pp. 1615-1622, CODEN:VISRAM: ISSN:0042-6989, (1984) Abstract only.
Noorwez et al., "Pharmacological chaperone-mediated in vivo folding and stabilization of the P23H-opsin mutant associated with autosomal dominant retinitis Pigmentosa", J. Biol. Chem., vol. 278. No. 16, pp. 14442-14450 (2003).
Noorwez et al., "Retinoids assist the cellular folding of the autosomal dominant retinitis Pigmentosa opsin mutant P23H", J. Biol. Chem., vol. 279, No. 16, pp. 16278-16284 (2004).
Norum and Blomhoff, "McCollum Award Lecture, 1992: Vitamin A absorption, transport, cellular uptake, and storage", Am. J. Clin. Nutr., vol. 56, pp. 735-744 (1992).
O'Byrne et al., "Retinoid adsorption and storage is impaired in mice lacking lecithin: retinol acyltransferase (LRAT)", J. Biol. Chem., vol. 280, pp. 35647-35657 (2005).
Owsley et al., "Delays in rod-mediated dark adaption in early age-related maculopathy", Ophthalmoloy, vol. 108, pp. 1196-1202 (2001).
Owsley et al., "Effect of short-term, high-dose retinol on dark adaption in agingand early age-related maculopathy", Invest. Ophthalmol. Vis. Sci., vol. 47, No. 4, pp. 1310-1318 (2006).
Paik et al., "9-cis-retinoids: biosynthesis of 9-cis-retinoic acid", Biochemistry, vol. 39, No. 27, pp. 8073-8084 (Jul. 2000) Abstract only.
Parry et al., "Visual pigment reconstitution in intact goldfish retina using synthetic retinaldehyde isomers", Vision research, vol. 40, No. 17, pp. 2241-2247 (2000).
Radomska et al., "The use of some ingredients for microemulsion preparation containing retinol and its esters", XP002475886, STN Database Accession No. 2000:139945 & International Journal of Pharmaceutics, vol. 196, No. 2, pp. 131-134 CODEN:IJPHEDI; ISSN; 0378-5173, (2000) Abstract only.
Rao et al., "Isomers of 3 7 11 trimethyldodeca-2 4 6 8 10-pentaenal A linear analog of retinal and lower homologues in their interaction

(56) References Cited

OTHER PUBLICATIONS with bovine opsin and bacterioopsin", Photochemistry and Photobiology, vol. 41, No. 2, pp. 171-174 (1985).
Rao et al., "5-(Trifluoromethyl)bacteriorhodopsin does not translocate protons", J. Am. Chem. Soc., vol. 108, pp. 6077-6078 (1986).
Rao et al., "Regioselective photo isomerisation of retinolacetate" Tetrahedron Letters, vol. 31, No. 24, pp. 3441-3444 (1990).
Redmond et al., "Rpe65 is necessary for production of 11-cis-vitamin A in the retinal visual cycle", Nature Genetics, vol. 20, pp, 344-351 (1998).
Reid et al., "Mass Spectral Analysis of Eleven Analogs of Vitamin A1", Lipids, vol. 8, No. 1, pp. 558-565 (1973).
Renk, "A rhodopsin pigment containing a spin-labeled retinal" J. Am. Chem. Soc., vol. 109, pp. 6163-6168 (1987).
Rezabek et al., "Effects of dietary retinyl acetate on the promotion of hepatic enzyme-altered foci by polybrominated biphenyls in initiated rats", Food Chem. Toxicol., vol. 27, No. 8, pp. 539-544 (1989) Abstract only.
Robinson et al., "Opsins with mutations at the site of chromophore attachment constitutively activate transducin but are not phosphorylated by rhodopsin kinase", Proc. Natl. Acad. Sci. USA, vol. 91, No. 12, pp. 5411-5415 (1994).
Rotenstreich et al., "Treatment of a retinal dystrophy, fundus albipunctatus, with oral 9-cis-b-carotene", Br. J. Opthalmol., vol. 94, pp. 616-621 (2010).
Russell, "The vitamin A spectrum: from deficiency to toxicity", Am. J. Clin. Nutr., vol. 71, pp. 878-884 (2000).
Saliba et al., "The cellular fat of mutant rhodopsin: quality control, degradation and aggresome formation", J. Cell Science, vol. 115, pp. 2907-2918 (2002).
Sandberg et al., "Clinical expression correlates with location of rhodopsin mutation in dominant retinitis Pigmentosa", Invest. Opthalmol. Vis. Sci., vol. 36, No. 9, pp. 1934-1942 (1995).
Sekiya et al., "Effect of modification of the chromophore in retinochrome" Biophysical Chemistry, vol. 56, pp. 31-39 (1995).
Semenova et al., "Systems for delivery of vitamin A to the retina in retinitis pigmentosa", XP002475884; STN Database Accession No. 2002:438129 & New Insights Into Retinal Degenerative Diseases, [Proceedings of the International Symposium on Retinal Degeneration], 9th, Durango, Co, United States, (2000), Meeting Date (2000), pp. 105-110; Editor (Anderson & Lavail), (2001) Abstract only.
Semenova et al., "Stabilization of all-trans-retinol bye cyclodestrins: a comparative study using HPLC and fluorescence spectroscopy", XP002475883; STN Database Acession No. 2003:494986 & Journal of Inclusion Phenomena and Macrocyclic Chemistry, Volume Date (2002), vol. 44, No. 1-4, pp. 155-158 CODEN:JIPCF5;ISSN:1388-3127, (2003) Abstract only.
Semple-Rowland et al., "A null mutation in the photoreceptor guanylate cyclase gene causes the retinal degeneration chicken phenotype", Proc. Natl. Acad. Sci. USA, vol. 95, No. 3, pp. 1271-1276 (1998).
Sen et al., "Synthesis and binding studies of a photoaffinity label for bovine rhodopsin", J. Am. Chem. Soc., vol. 104, pp. 3214-3216 (1982).
Sibulesky et al., "Safety of<7500 RE (<25000 IU) vitamin A daily in adults with retinitis Pigmentosa", Am. J. Clin. Nutr., vol. 69, pp. 656-663 (1999).
Sokal et al., "GCAP1 (Y99C) mutant is constitutively active in autosomal dominant cone dystrophy", Mol. Cell. vol. 2, No. 1, pp. 129-133 (1998).
Spaeth, "Ophthalmic Surgery: Principles & Practice, Second Edition", Harcourt Brace Jovanich, Inc. pp. 85-99 (1990).
Stecher et al., "Preferential release *11-cis-retinol* from retinal pigment epithelial cells in the presence of cellular retinaldehyde-binding protein" The Journal of Biological Chemistry, vol. 274, No. 13, pp. 8577-8585 (1999).
Steinberg et al., "Isomer composition and spectra of the dark and light adapted forms of artificial bacteriorhodopsins", Photochemistry and Photobiology, vol. 54, No. 6, pp. 969-976 (1991).

Supplementary European Search Report From Related European Patent Application No. EP 05773576, mailed on Aug. 4, 2008.
Tan et al., "Absolute sense of twist of the C12—C13 bond of the retinal chromophorein bovine rhodopsin based on excitor-coupled CD spectra of 11, 12-dihydroretinal analogues", Angew. Chem. Int. Ed. Engl. vol. 36, No. 19, pp. 2089-2093 (1997).
Tarkhov et al., "Study of a structure-property relationship for retinal derivatives taking into account their conformational flexibility", Chemical Abstracts, vol. 128, No. 18, pp. 270 (1998) Abstract No. 128:214600 Abstract only.
Teller et al., "Advances in determination of a high-resolution three-dimensional structure of rhodopsin, a model of G-protein-coupled receptors (GPCRs)", Biochemistry vol. 40, No. 26, pp. 7761-7772 (2001).
The Eye Digest, "Aging eye in the US", 2 pgs. (2011) printed from http://web.archive.org/web/20060810014820/http://www.agingeye.net/mainnews/usaging.php.
Thomson Scientific London, GB; AN 1995-063773, XP002475888 & JP 06340525 A (Lion Corp); Dec. 13, 1993 Abstract only.
Thomson Scientific, London, GB: AN 1996-408307, XP002475889 & JP 08198746 A (Lion Corp); Aug. 6, 1996 Abstract only.
Thomson Scientific, London, GB; AN 1998-518867, XP002475890 & RU 2106813 C1 (Krasy Med. Acad); Mar. 20, 1998 Abstract only.
Thompson et al., "Mutations in the gene encoding lecithin retinol acyltransferase are associated with early-onset severe retinal dystrophy", Nat. Genet., vol. 28, pp. 123-124 (2001).
Thompson et al., "Gene defects in vitamin A metabolism of the retinal pigment epithelium", Genetics in Ophthalmology, vol. 37, pp. 141-154 (2003).
Travis et al.. "Diseases caused by defects in the visual cycle: retinoids as potential therapeutic agents", Annu. Rev. Pharmacol. Toxicol., vol. 47, pp. 469-512 (2007).
Van Hooser et al., "Rapid restoration of visual pigment and function with oral retinoid in a mouse model of childhood blindness", PNAS, vol. 97, No. 15, pp. 8623-8628 (2000).
Van Hooser et al., "Recovery of visual functions in a mouse model of leber congenital amaurosis", The Journal of Biological Chemistry, vol. 277, No. 21, pp. 19173-19182 (2002).
Vitamin Converter, known vitamin A conversion, 3 pgs., printed from http://www.robert-forbes.com/resources/vitaminconverter.html on Apr. 19, 2012.
Wada et al,, "Retinoids and related compounds. part 26. synthesis of (11Z)-8, 18-propano- and methano-retinals and conformational study of the rhodopsin chromophore", J. Chem. Soc., vol. 1, pp. 2430-2439 (2001).
Weiser and Somorjai, "Bioactivity of cis and dicis isomers of vitamin A esters", Internatl. J. Vit. Nutr., vol. 62, pp. 201-208 (1992).
Wingerath et al.. "Analysis of cyclic and acyclic analogs of retinol, retinoic acid, and retinal by laser desorption Ionization-, matrix-assisted laser desorption ionization-mass spectroscopy and UV/Vis spectroscopy", Analytical Biochemistry, vol. 272, pp. 232-242 (1999).
Witkovsky et al,, "Formation, conversion, and utilization of isorhodopsin, rhodopsin, and porphyropsin by rod photoreceptors in the xenopus retina", J. Gen. Physiol., vol. 72, pp. 821-836 (1978).
www.wrongdiagnosis.com. "Symptom: night blindness", pp. 1-13 (Jun. 3, 2008).
Woodward et al.. "The inflow and outflow of anti-glaucoma frugs", Trends Pharm. Sci., vol. 25, Issue 5, pp. 238-241 (2004).
Yamamoto et al., "Important role of the proline residue in the signal sequence that directs the secretion of human lysozyme in *Saccharomyces cerevisiae*", Biochemistry, vol. 28, pp. 2728-2732 (1989).
Yamamoto et al., "Mutations in the gene encoding 11-cis retinol dehydrogenase cause delayed dark adaptation and fundus Albipunctatus", Nat. Genet., vol. 22, No. 2, pp. 188-191 (1999).
Yan et al., "Mechanism of activation of sensory rhodopsin I: evidence for a steric trigger", PNAS, vol. 88, pp. 9412-9416 (1991).
Yoshikami et al., "Visual pigments of vitamin A-deficient rat following vitamin A2 administration", Vision Research, vol. 9, No. 6, pp. 633-636 (1969).
Yoshizawa and Wald, "Photochemistry of Iodopsin", Nature vol. 214, pp. 566-571 (1967).

(56) References Cited

OTHER PUBLICATIONS

Zankel et al., "Bovine rhodopsin with 11-cis-locked retinal chromophore neither activates rhodopsin kinase nor undergoes conformational change upon irradiation", J. American Chemical Soc., vol. 112, No. 13, pp. 5387-5388 (1990).

Zhang et al., "Structure, alternative splicing, and expression of the human RGS9 gene", Gene, vol. 240, No. 1, pp. 23-24 (1999).

Zhu et al., "A naturally occurring mutation of the opsin gene (T4R) in dogs affects glycosylation and stability of the G protein-coupled receptor", J. Biol. Chem., vol. 279, No. 51, pp. 53828-53839 (2004).

Ames et al., "Biomedical studies on vitamin A. XIV. Biopotencies of Geometric isomers of Vitamin in the Rat", J. Am. Chem. Soc., vol. 77. pp. 4134-4136 (1955).

Chan et al., "Delayed dark adaption caused by nilutamide", J. Neuro-Opthalmology, vol. 28, No. 2, pp. 158-159 (2008).

Gaffney et al., "Acing and cone dark adaptation", Optom. Vis. Sci , vol. 89, No. 8, pp. 1219-1224 (2012).

Marmor et al., "Abipunctate retinopathy with cone dysfunction and no abnormality in RDH5 or RLBP1 genes", Retina, vol. 23, No. 4, pp. 543-546 (2003).

Morimura et al., "Mutations in the RPE65 gene in patients with autosomal recessive retinitis pigmentosa or Leber congenital amaurosis", PNAS USA, vol. 95, pp. 3088-3093 (1998).

Remington: The Science and Practice of Pharmacy, 19$^{th}$ Edition, Gennaro et al., Ed., Mack Publishing Company, pp. 1528-1529 (1995).

Chen et al., "Inherent instability of the retinitis pigmentosa P23H mutant opsin", JBC Papers in Press, Manuscript M114.551713, 31 pages, Latest version can be accessed at http://www.jbc.org/cgi/doi/10.1074/jbc.M114.551713, Published Feb. 10, 2014.

Koenekoop et al., "Oral 9-cis retinoid for childhood blindness due to Leber congenital amaurosis caused by RPE65 or LRAT mutations: an open-label phase 1b trial", Lancet, 8 pages, Published Online http://dx.doi.org/10.1016/S0140-6736(14)60153-7, Published Jul. 14, 2014.

Maeda et al., "QLT091001, a 9-cis-retinal analog, is well-tolerated by retinas of mice with impaired visual cycles", Invest. Opthalmol. Vis. Sci., vol. 54, No. 1, pp. 455-466 (2013).

Mendes et al., "Pharmacological manipulation of rhodopsin retinitis pigmentosa", Advances in Experimental Medicine and Biology, Chapter 36, pp. 317-323, DOI 10.1007/978-1-4419-1399-9_36, Springer Science+Business Media, LLC (2010).

Sakami et al., "Probing mechanisms of photoreceptor degeneration in a new mouse model of the common form of autosomal dominant retinitis pigmentosa due to P23H opsin mutations", JBC Papers in Press, Manuscript M110.209759, 29 pages, Latest version can be accessed at http://www.jbc.org/cgi/doi/10.1074/jbc.M110.209759, Published Jan. 11, 2011.

Kuse et al., "Chang in rod cell function y age-related macular degeneration", Japanese Review of Clinical Ophthalmology, vol. 10, No. 100, pp. 59 (2006) English Abstract.

Price et al., "Mislocation and degradation of human P23H-Rhodopsin-GFP in a knockin mouse model of retinitis pigmentosa", Inv. Opth. Vis. Sci., vol. 52, No. 13, pp. 9728-9736 (2011).

Rotenstreich et al., "Treatment with 9-cis β-carotene-rich powder in patients with retinitis pigmentosa: a randomized crossover trial", JAMA Ophthalmol., vol. 131, No. 8, pp. 985-992 (2013).

"Types of AMD", Macular Degeneration Partnership, 8733 Beverly Blvd., Suite201, Los Angeles, CA 90048, Online article downloaded from: http://web.archive.org/web/20030216034002/http://www.amd.org/amd/typesofamd.asp, 3 pages (2003).

"What is AMD?", Macular Degeneration Partnership, 8733 Beverly Blvd., Suite201, Los Angeles, CA 90048, Online article downloaded from: http://web.archive.org/web/20030206231257/http://amd.org/amd/index.asp, 2 pages (2003).

\* cited by examiner

RETINAL DERIVATIVES AND METHODS FOR THE USE THEREOF FOR THE TREATMENT OF VISUAL DISORDERS

CROSS-REFERENCE TO RELATED APPLICATIONS

This application is a continuation of U.S. patent application Ser. No. 13/042,308, filed Mar. 7, 2011, which claims the benefit of priority to U.S. patent application Ser. No. 11/629,875, now U.S. Pat. No. 7,951,841, filed Feb. 12, 2008, under 35 U.S.C. §371(c) (1) as a U.S. national stage entry of International Patent Application No. PCT/US2005/021812, filed Jun. 20, 2005 under the Patent Cooperation Treaty, and claims the benefit of priority to U.S. Provisional Patent Application No. 60/580,889, filed Jun. 18, 2004, each of which is incorporated herein by reference in its entirety.

STATEMENT REGARDING GOVERNMENT INTEREST

This research was supported by United States Public Health Service Grant EY09339 from the National Eye Institute of the National Institutes of Health. The Government has certain rights in the invention.

BACKGROUND OF THE INVENTION

A diminished visual acuity or total loss of vision may result from a number of eye diseases or disorders caused by dysfunction of tissues or structures in the anterior segment of the eye and/or posterior segment of the eye. Disease or disorders of the posterior segment of the eye in general are retinal or choroidal vascular diseases or hereditary diseases such as Leber Congenital Amaurosis. Age related macular degeneration (AMD) is one of the specific diseases associated with the posterior portion of the eyeball and is the leading cause of blindness among older people. AMD results in damage to the macula, a small circular area in the center of the retina. Because the macula is the area which enables one to discern small details and to read or drive, its deterioration may bring about diminished visual acuity and even blindness. The retina contains two forms of light receiving cells, rods and cones, that change light into electrical signals. The brain then converts these signals into the images. The macula is rich in cone cells, which provides central vision. People with AMD suffer deterioration of central vision but usually retain peripheral sight.

Slightly blurred or distorted vision is the most common early symptom of AMD. Visual loss with dry AMD usually progresses slowly while visual loss with wet AMD proceeds more rapidly and may occur over days or weeks. Patients who have wet AMD in one eye are at increased risk of developing choroidal neo-vascularization (CNV) in the other eye. The magnitude of the risk varies, depending on the appearance of the second eye. The risk is greater in eyes with numerous large drusen, with abnormal pigment changes in the macula, and in patients with a history of high blood pressure. Reactions that go on in the RPE lead to oxidative products leading to cell death and neovascularization. This excess metabolism leads to the formation of drusen under the RPE.

Other eye diseases also affect photoreceptor function in the eye. Retinitis Pigmentosa represents disease caused by defects in many different genes. They all have a final common pathway of night blindness and peripheral vision loss that can lead to narrowing of the visual field and eventual loss of all vision in many patients. The rod photoreceptors are usually primarily affected and most of the gene defects leading to the disease occur in genes that are expressed predominantly or only in the rod cells.

One autosomal dominant form of Retinitis Pigmentosa comprises an amino acid substitution in opsin, a proline to histidine substitution at amino acid 23. This defect compromises 10-20% of all Retinitis Pigmentosa cases. This abnormal opsin protein forms a protein aggregate that eventually leads to cell death.

Leber Congenital Amaurosis is a very rare childhood condition that affects children from birth or shortly thereafter. It affects both rods and cones. There are a few different gene defects that have been associated with the disease. These include the genes encoding the RPE65 and LRAT proteins. Both result in a person's inability to make 11-cis-retinal in adequate quantities. In the RPE65-defective individuals, retinyl esters build up in the retinal pigment epithelium (RPE). LRAT-defective individuals are unable to make esters and subsequently secrete any excess retinoids.

Retinitis Punctata Albesciens is another form of Retinitis Pigmentosa that exhibits a shortage of 11-cis-retinal in the rods. Aging also leads to the decrease in night vision and loss of contrast sensitivity due to a shorting of 11-cis-retinal. Excess unbound opsin is believed to randomly excite the visual transduction system. This can create noise in the system, and thus more light and more contrast is necessary to see well.

Congenital Stationary Night Blindness (CSNB) and Fundus Albipunctatus are a group of diseases that are manifested as night blindness, but there is not a progressive loss of vision as in the Retinitis Pigmentosa. Some forms of CSNB are due to a delay in the recycling of 11-cis-retinal. Fundus Albipunctatus until recently was thought to be a special case of CSNB where the retinal appearance is abnormal with hundreds of small white dots appearing in the retina. It has been shown recently that this is also a progressive disease although much slower than Retinitis Pigmentosa. It is caused by a gene defect that leads to a delay in the cycling of 11-cis-retinal.

Currently, there are few treatments for retinoid deficiency. One treatment, a combination of antioxidant vitamins and zinc, produces only a small restorative effect. Thus, there is a need for compositions and methods of restoring or stabilizing photoreceptor function and ameliorating the effects of deficient levels of endogenous retinoids.

BRIEF SUMMARY OF THE INVENTION

The present invention provides compounds and methods of using such compound to restore and/or stabilize photoreceptor function in a vertebrate visual system. Synthetic retinal derivatives can be administered to human or non-human vertebrate subjects to restore or stabilize photoreceptor function, and/or to ameliorate the effects of a deficiency in retinoid levels.

In one aspect, synthetic retinal derivatives are provided. The synthetic retinal derivative can be, for example, a derivative of Formula I, II, III, IV, V, VI, VII, VIII, IX, X, XI, XII, XIII, XIV, XV and/or XVI. In some embodiments, the synthetic retinal derivatives is a retinyl ester, such as a 9-cis-retinyl ester or an 11-cis-retinyl ester. The ester substituent can be, for example, a carboxylate radical of a $C_3$ to $C_{22}$ polycarboxylic acid (polycarboxylate). For example, the substituent can be succinate, citrate, ketoglutarate, fumarate, malate and oxaloacetate. In some embodiments, the ester substituent is not tartarate.

In some embodiments, the retinyl ester is a 9-cis-retinyl ester of a $C_3$ to $C_{22}$ carboxylate. In other embodiments, the retinyl ester is a 9-cis-retinyl ester of a $C_3$ to $C_{10}$ carboxylate. In some embodiments, the retinyl ester is an 11-cis-retinyl ester of a $C_3$ to Cu carboxylate. In other embodiments, the retinyl ester is an 11-cis-retinyl ester of a $C_3$ to $C_{10}$ carboxylate.

Also provided are pharmaceutical compositions comprising the synthetic retinal derivative and a pharmaceutically acceptable vehicle. The synthetic retinal derivative can be, for example, a derivative of Formula I, II, III, IV, V, VI, VII, VIII, IX, X, XI, XII, XIII, XIV, XV and/or XVI. In some embodiments, the synthetic retinal derivatives is a retinyl ester, such as a 9-cis-retinyl ester or an 11-cis-retinyl ester. The ester substituent can be, for example, a carboxylate radical of a $C_3$ to $C_{22}$ polycarboxylic acid. The pharmaceutical composition can be compounded, for example, as an ophthalmological composition in an ophthalmologically acceptable vehicle for administration to the eye topically or by intra-ocular injection.

In another aspect, a method of restoring photoreceptor function in a mammal is provided. The method includes administering to a mammalian subject having an endogenous retinoid deficiency an effective amount of a synthetic retinal derivative, wherein the synthetic retinal derivative is converted into a retinal capable of forming a functional opsin/retinal complex. The synthetic retinal derivative can be, for example, a 9-cis-retinyl ester, an 11-cis-retinyl ester, or a combination thereof. The ester substituent can be a carboxylate radical of a $C_1$-$C_{10}$ monocarboxylic acid or a $C_2$ to $C_{22}$ polycarboxylic acid. In some embodiments, synthetic retinal derivative is 9-cis-retinyl acetate or 11-cis-retinyl acetate. In other embodiments, the ester substituent comprises a carboxylate radical of a polycarboxylic acid of $C_3$ to $C_{10}$. For example, the ester substituent can be succinate, citrate, ketoglutarate, fumarate, malate and oxaloacetate. The mammalian subject can be, for example, human or other mammal.

In another aspect, a method of ameliorating loss of photoreceptor function in a mammal is provided. The method includes administering an effective amount of a synthetic retinal derivative to the vertebrate eye, wherein the synthetic retinal derivative is converted into a retinal capable of forming a functional opsin/retinal complex. The synthetic retinal derivative can be, for example, a 9-cis-retinyl ester, an 11-cis-retinyl ester, or a combination thereof. The ester substituent canoe a carboxylate radical of a $C_1$-$C_{10}$ monocarboxylic acid or a $C_2$ to $C_{22}$ polycarboxylic acid. In some embodiments, synthetic retinal derivative is 9-cis-retinyl acetate or 11-cis-retinyl acetate. In other embodiments, the ester substituent comprises a carboxylate radical of a polycarboxylic acid of $C_3$ to $C_{10}$. For example, the ester substituent can be succinate, citrate, ketoglutarate, fumarate, malate and oxaloacetate. The mammalian subject can be, for example, human or other mammal.

In an aspect, a method of restoring photoreceptor function in a vertebrate eye is provided. The method can include administering to the vertebrate in need thereof having an endogenous retinoid deficiency an effective amount of a synthetic retinal derivative in a pharmaceutically acceptable vehicle, wherein the synthetic retinal derivative is converted into a retinal capable of forming a functional opsin/retinal complex. The synthetic retinal derivative can be, for example, a derivative of Formula I, II, III, IV, V, VI, VII, VIII, IX, X, XI, XII, XIII, XIV, XV and/or XVI. In some methods, if the synthetic retinal derivative is a 9-cis-retinyl ester comprising a monocarboxylic acid ester substituent, it is a 9-cis-retinyl $C_1$ to $C_{10}$ ester. In some methods, if the synthetic retinal derivative is an 11-cis-retinyl ester comprising a monocarboxylic acid ester substituent, it is an 11-cis-retinyl $C_1$ to $C_{10}$ ester.

In some methods, the synthetic retinal derivative is a 9-cis-retinyl ester, such as, for example, 9-cis-retinyl acetate, 9-cis-retinyl succinate, 9-cis-retinyl citrate, 9-cis-retinyl ketoglutarate, 9-cis-retinyl fumarate, 9-cis-retinyl malate, 9-cis-retinyl oxaloacetate, or the like. In some methods, the synthetic retinal derivative is an 11-cis-retinyl ester, such as, for example, 11-cis-retinyl acetate, 11-cis-retinyl succinate, 11-cis-retinyl citrate, 11-cis-retinyl ketoglutarate, 11-cis-retinyl fumarate, 11-cis-retinyl malate, 11-cis-retinyl oxaloacetate, or the like.

In some methods, the synthetic retinal derivative can be administered to a vertebrate in need thereof. For example, the vertebrate can have, or be predisposed to developing, an endogenous retinoid deficiency associated with Age-Related Macular Degeneration, Leber Congenital Amaurosis, Retinitis Punctata Albesciens, Congenital Stationary Night Blindness, Fundus Albipunctatus, or other disease or condition associated with an endogenous retinoid deficiency.

In some methods, the synthetic retinoid derivative can be administered locally, such as by eye drops, intraocular injection, periocular injection or the like. In other methods, the synthetic retinal derivative can be orally administered to the vertebrate. In some methods, the vertebrate is a human.

In another aspect, a method of sparing the requirement for endogenous retinoid in a vertebrate eye is provided. The method can include administering to the eye a synthetic retinal derivative in a pharmaceutically or ophthalmologically acceptable vehicle, wherein the synthetic retinal derivative is converted into a retinal capable of forming a functional opsin/retinal complex. The synthetic retinal derivative can be, for example, a derivative of Formula I, II, III, IV, V, VI, VII, VIII, IX, X, XI, XII, XIII, XIV, XV and/or XVI. In some methods, if the synthetic retinal derivative is a 9-cis-retinyl ester comprising a monocarboxylic acid ester substituent, it is a 9-cis-retinyl $C_1$ to $C_{10}$ ester. In some methods, if the synthetic retinal derivative is an 11-cis-retinyl ester comprising a monocarboxylic acid ester substituent, it is an 11-cis-retinyl $C_1$ to $C_{10}$ ester.

In some methods, the synthetic retinal derivative is a 9-cis-retinyl ester, such as, for example, 9-cis-retinyl acetate, 9-cis-retinyl succinate, 9-cis-retinyl citrate, 9-cis-retinyl ketoglutarate, 9-cis-retinyl fumarate, 9-cis-retinyl malate, 9-cis-retinyl oxaloacetate, or the like. In some methods, the synthetic retinal derivative is an 11-cis-retinyl ester, such as, for example, 11-cis-retinyl acetate, 11-cis-retinyl succinate, 11-cis-retinyl citrate, 11-cis-retinyl ketoglutarate, 11-cis-retinyl fumarate; 11-cis-retinyl malate, 11-cis-retinyl oxaloacetate, or the like.

In some methods, the synthetic retinal derivative can be administered to a vertebrate in need thereof. For example, the vertebrate can have, or be predisposed to developing, an endogenous retinoid deficiency associated with Age-Related Macular Degeneration, Leber Congenital Amaurosis, Retinitis Punctata Albesciens, Congenital Stationary Night Blindness, Fundus Albipunctatus, or other disease or condition associated with an endogenous retinoid deficiency.

In some methods, the synthetic retinoid derivative can be administered locally, such as by eye drops, intraocular injection, periocular injection or the like. In other methods, the synthetic retinal derivative can be orally administered to the vertebrate. In some methods, the vertebrate is a human.

In yet another aspect, a method of ameliorating loss of photoreceptor function in a vertebrate eye is provided. The method can include prophylactically administering an effective amount of a synthetic retinal derivative in a pharmaceutically or ophthalmologically acceptable vehicle to the vertebrate eye, wherein the synthetic retinal derivative is converted into a retinal capable of forming a functional opsin/retinal complex. The synthetic retinal derivative can be, for example, a derivative of Formula I, II, III, IV, V, VI, VII, VIII, IX, X, XI, XII, XIII, XIV, XV and/or XVI. In some methods, if the synthetic retinal derivative is a 9-cis-retinyl ester comprising a monocarboxylic acid ester substituent, it is a 9-cis-retinyl $C_1$ to $C_{10}$ ester. In some methods, if the synthetic retinal derivative is an 11-cis-retinyl ester comprising a monocarboxylic acid ester substituent, it is an 11-cis-retinyl $C_1$ to $C_{10}$ ester.

In some methods, the synthetic retinal derivative is a 9-cis-retinyl ester, such as, for example, 9-cis-retinyl acetate, 9-cis-retinyl succinate, 9-cis-retinyl citrate, 9-cis-retinyl ketoglutarate, 9-cis-retinyl fumarate, 9-cis-retinyl malate, 9-cis-retinyl oxaloacetate, or the like. In some methods, the synthetic retinal derivative is an 11-cis-retinyl ester, such as, for example, 11-cis-retinyl acetate, 11-cis-retinyl succinate, 11-cis-retinyl citrate, 11-cis-retinyl ketoglutarate, 11-cis-retinyl fumarate, 11-cis-retinyl malate, 11-cis-retinyl oxaloacetate, or the like.

In some methods, the synthetic retinoid derivative can be administered locally, such as by eye drops, intraocular injection, periocular injection or the like. In other methods, the synthetic retinal derivative can be orally administered to the vertebrate. In some methods, the vertebrate is a human.

In yet a further aspect, a method of selecting a treatment for a subject having diminished visual capacity is provided. The method can include determining whether the subject has a deficient endogenous retinoid level, as compared with a standard subject; and administering to the subject an effective amount of a synthetic retinal derivative in a pharmaceutically acceptable vehicle (e.g., an ophthalmologically acceptable vehicle), wherein the synthetic retinal derivative is converted into a retinal capable of forming a functional opsin/retinal complex. The synthetic retinal derivative can be, for example, a derivative of Formula I, II, III, IV, V, VI, VII, VIII, IX, X, XI, XII, XIII, XIV, XV and/or XVI. In some methods, if the synthetic retinal derivative is a 9-cis-retinyl ester comprising a monocarboxylic acid ester substituent, it is a 9-cis-retinyl $C_1$ to $C_{10}$ ester. In some methods, if the synthetic retinal derivative is an 11-cis-retinyl ester comprising a monocarboxylic acid ester substituent, it is an 11-cis-retinyl $C_1$ to $C_{10}$ ester.

In some methods, the synthetic retinal derivative is a 9-cis-retinyl ester, such as, for example, 9-cis-retinyl acetate, 9-cis-retinyl succinate, 9-cis-retinyl citrate, 9-cis-retinyl ketoglutarate, 9-cis-retinyl fumarate, 9-cis-retinyl malate, 9-cis-retinyl oxaloacetate, or the like. In some methods, the synthetic retinal derivative is an 11-cis-retinyl ester, such as, for example, 11-cis-retinyl acetate, 11-cis-retinyl succinate, 11-cis-retinyl citrate, 11-cis-retinyl ketoglutarate, 11-cis-retinyl fumarate, 11-cis-retinyl malate, 11-cis-retinyl oxaloacetate, or the like.

In some methods, the endogenous retinoid is an 11-cis-retinyl ester. In some methods, the synthetic retinoid derivative can be administered locally, such as by eye drops, intraocular injection, periocular injection or the like. In other methods, the synthetic retinal derivative can be orally administered to the vertebrate. In some methods, the vertebrate is a human.

In yet a further aspect, pharmaceutical compositions and oral dosage forms are provided. The compositions can include a synthetic retinal derivative in a pharmaceutically acceptable vehicle (e.g., an ophthalmologically acceptable vehicle). The synthetic retinal derivative can be, for example, a derivative of Formula I, II, III, IV, V, VI, VII, VIII, IX, X, XI, XII, XIII, XIV, XV and/or XVI. In some methods, if the synthetic retinal derivative is a 9-cis-retinyl ester comprising a monocarboxylic acid ester substituent, it is a 9-cis-retinyl $C_1$ to $C_{10}$ ester. In some methods, if the synthetic retinal derivative is an 11-cis-retinyl ester comprising a monocarboxylic acid ester substituent, it is an 11-cis-retinyl $C_1$ to $C_{10}$ ester.

In some methods, the synthetic retinal derivative is a 9-cis-retinyl ester, such as, for example, 9-cis-retinyl acetate, 9-cis-retinyl succinate, 9-cis-retinyl citrate, 9-cis-retinyl ketoglutarate, 9-cis-retinyl fumarate, 9-cis-retinyl malate, 9-cis-retinyl oxaloacetate, or the like. In some methods, the synthetic retinal derivative is an 11-cis-retinyl ester, such as, for example, 11-cis-retinyl acetate, 11-cis-retinyl succinate, 11-cis-retinyl citrate, 11-cis-retinyl ketoglutarate, 11-cis-retinyl fumarate, 11-cis-retinyl malate, 11-cis-retinyl oxaloacetate, or the like.

The pharmaceutical composition can be, for example, an intraocular injectable solution or a periocular injectable solution. The oral dosage form can be, for example, a pill, tablet, capsule, gel cap, or the like.

In yet another aspect, a method of treating Leber Congenital Amaurosis in a human subject is provided. The method generally includes administering to a subject in need thereof an effective amount of a synthetic retinal derivative in a pharmaceutically or ophthalmologically acceptable vehicle. The synthetic retinal derivative can be, for example, a derivative of Formula I, II, III, IV, V, VI, VII, VIII, IX, X, XI, XII, XIII, XIV, XV and/or XVI. In some methods, if the synthetic retinal derivative is a 9-cis-retinyl ester comprising a monocarboxylic acid ester substituent, it is a 9-cis-retinyl $C_1$ to $C_{10}$ ester. In some methods, if the synthetic retinal derivative is an 11-cis-retinyl ester comprising a monocarboxylic acid ester substituent, it is an 11-cis-retinyl $C_1$ to $C_{10}$ ester.

In some methods, the synthetic retinal derivative is a 9-cis-retinyl ester, such as, for example, 9-cis-retinyl acetate, 9-cis-retinyl succinate, 9-cis-retinyl citrate, 9-cis-retinyl ketoglutarate, 9-cis-retinyl fumarate, 9-cis-retinyl malate, 9-cis-retinyl oxaloacetate, or the like. In some methods, the synthetic retinal derivative is an 11-cis-retinyl ester, such as, for example, 11-cis-retinyl acetate, 11-cis-retinyl succinate, 11-cis-retinyl citrate, 11-cis-retinyl ketoglutarate, 11-cis-retinyl fumarate, 11-cis-retinyl malate, 11-cis-retinyl oxaloacetate, or the like.

In some methods, the synthetic retinoid derivative can be administered locally, such as by eye drops, intraocular injection, periocular injection or the like. In other methods, the synthetic retinal derivative can be orally administered to the vertebrate. In some methods, the vertebrate is a human.

In another aspect, a method of treating Retinitis Punctata Albesciens, Congenital Stationary Night Blindness or Fundus Albipunctatus in a human subject is provided. The method can include administering to the subject in need thereof an effective amount of a synthetic retinal derivative in a pharmaceutically or ophthalmologically acceptable vehicle. The method generally includes administering to a subject in need thereof an effective amount of a synthetic retinal derivative in a pharmaceutically or ophthalmologically acceptable vehicle. The synthetic retinal derivative can be, for example, a derivative of Formula I, II, III, IV, V, VI, VII, VIII, IX, X, XI, XII, XIII, XIV, XV and/or XVI. In some methods, if the synthetic retinal derivative is a 9-cis-retinyl ester comprising a monocarboxylic acid ester substituent, it is a 9-cis-retinyl $C_1$ to $C_{10}$ ester. In some methods, if the synthetic retinal derivative is an 11-cis-retinyl ester comprising a monocarboxylic acid ester substituent, it is an 11-cis-retinyl $C_1$ to $C_{10}$ ester.

In some methods, the synthetic retinal derivative is a 9-cis-retinyl ester, such as, for example, 9-cis-retinyl acetate, 9-cis-retinyl succinate, 9-cis-retinyl citrate, 9-cis-retinyl ketoglutarate, 9-cis-retinyl fumarate, 9-cis-retinyl malate, 9-cis-retinyl oxaloacetate, or the like. In some methods, the synthetic retinal derivative is an 11-cis-retinyl ester, such as, for example, 11-cis-retinyl acetate, 11-cis-retinyl succinate, 11-cis-retinyl citrate, 11-cis-retinyl ketoglutarate, 11-cis-retinyl fumarate, 11-cis-retinyl malate, 11-cis-retinyl oxaloacetate, or the like.

In some methods, the synthetic retinoid derivative can be administered locally, such as by eye drops, intraocular injection, periocular injection or the like. In other methods, the synthetic retinal derivative can be orally administered to the vertebrate. In some methods, the vertebrate is a human.

In yet another aspect, a method of treating Age-Related Macular Degeneration in a human subject is provided. The method can include administering to the subject in need thereof an effective amount of a synthetic retinal derivative in a pharmaceutically or ophthalmologically acceptable vehicle. The synthetic retinal derivative can be, for example, a derivative of Formula I, II, III, IV, V, VI, VII, VIII, IX, X, XI, XII, XIII, XIV, XV and/or XVI. In some methods, if the synthetic retinal derivative is a 9-cis-retinyl ester comprising a monocarboxylic acid ester substituent, it is a 9-cis-retinyl $C_1$ to $C_{10}$ ester. In some methods, if the synthetic retinal derivative is an 11-cis-retinyl ester comprising a monocarboxylic acid ester substituent, it is an 11-cis-retinyl $C_1$ to $C_{10}$ ester.

In some methods, the synthetic retinal derivative is converted into a synthetic retinal that binds to free opsin in the eye. In some methods, the synthetic retinal derivative is a 9-cis-retinyl ester, such as, for example, 9-cis-retinyl acetate, 9-cis-retinyl succinate, 9-cis-retinyl citrate, 9-cis-retinyl ketoglutarate, 9-cis-retinyl fumarate, 9-cis-retinyl malate, 9-cis-retinyl oxaloacetate, or the like. In some methods, the synthetic retinal derivative is an 11-cis-retinyl ester, such as, for example, 11-cis-retinyl acetate, 11-cis-retinyl succinate, 11-cis-retinyl citrate, 11-cis-retinyl ketoglutarate, 11-cis-retinyl fumarate, 11-cis-retinyl malate, 11-cis-retinyl oxaloacetate, or the like.

In some methods, the synthetic retinoid derivative can be administered locally, such as by eye drops, intraocular injection, periocular injection or the like. In other methods, the synthetic retinal derivative can be orally administered to the vertebrate. In some methods, the vertebrate is a human.

In yet a further aspect, a method of treating or preventing loss of night vision or contrast sensitivity in an aging human subject is provided. The method can include administering to the subject in need thereof an effective amount of a synthetic retinal derivative in a pharmaceutically or ophthalmologically acceptable vehicle. The synthetic retinal derivative can be, for example, a derivative of Formula I, II, III, IV, V, VI, VII, VIII, IX, X, XI, XII, XIII, XIV, XV and/or XVI. In some methods, if the synthetic retinal derivative is a 9-cis-retinyl ester comprising a monocarboxylic acid ester substituent, it is a 9-cis-retinyl $C_1$ to $C_{10}$ ester. In some methods, if the synthetic retinal derivative is an 11-cis-retinyl ester comprising a monocarboxylic acid ester substituent, it is an 11-cis-retinyl $C_1$ to $C_{10}$ ester.

In some methods, the synthetic retinal derivative is converted into a synthetic retinal that binds to free opsin in the eye. In some methods, the synthetic retinal derivative is a 9-cis-retinyl ester, such as, for example, 9-cis-retinyl acetate, 9-cis-retinyl succinate, 9-cis-retinyl citrate, 9-cis-retinyl ketoglutarate, 9-cis-retinyl fumarate, 9-cis-retinyl malate, 9-cis-retinyl oxaloacetate, or the like. In some methods, the synthetic retinal derivative is an 11-cis-retinyl ester, such as, for example, 11-cis-retinyl acetate, 11-cis-retinyl succinate, 11-cis-retinyl citrate, 11-cis-retinyl ketoglutarate, 11-cis-retinyl fumarate, 11-cis-retinyl malate, 11-cis-retinyl oxaloacetate, or the like.

In some methods, the synthetic retinoid derivative can be administered locally, such as by eye drops, intraocular injection, periocular injection or the like. In other methods, the synthetic retinal derivative can be orally administered to the vertebrate. In some methods, the vertebrate is a human.

DETAILED DESCRIPTION OF THE INVENTION

Figure 1:
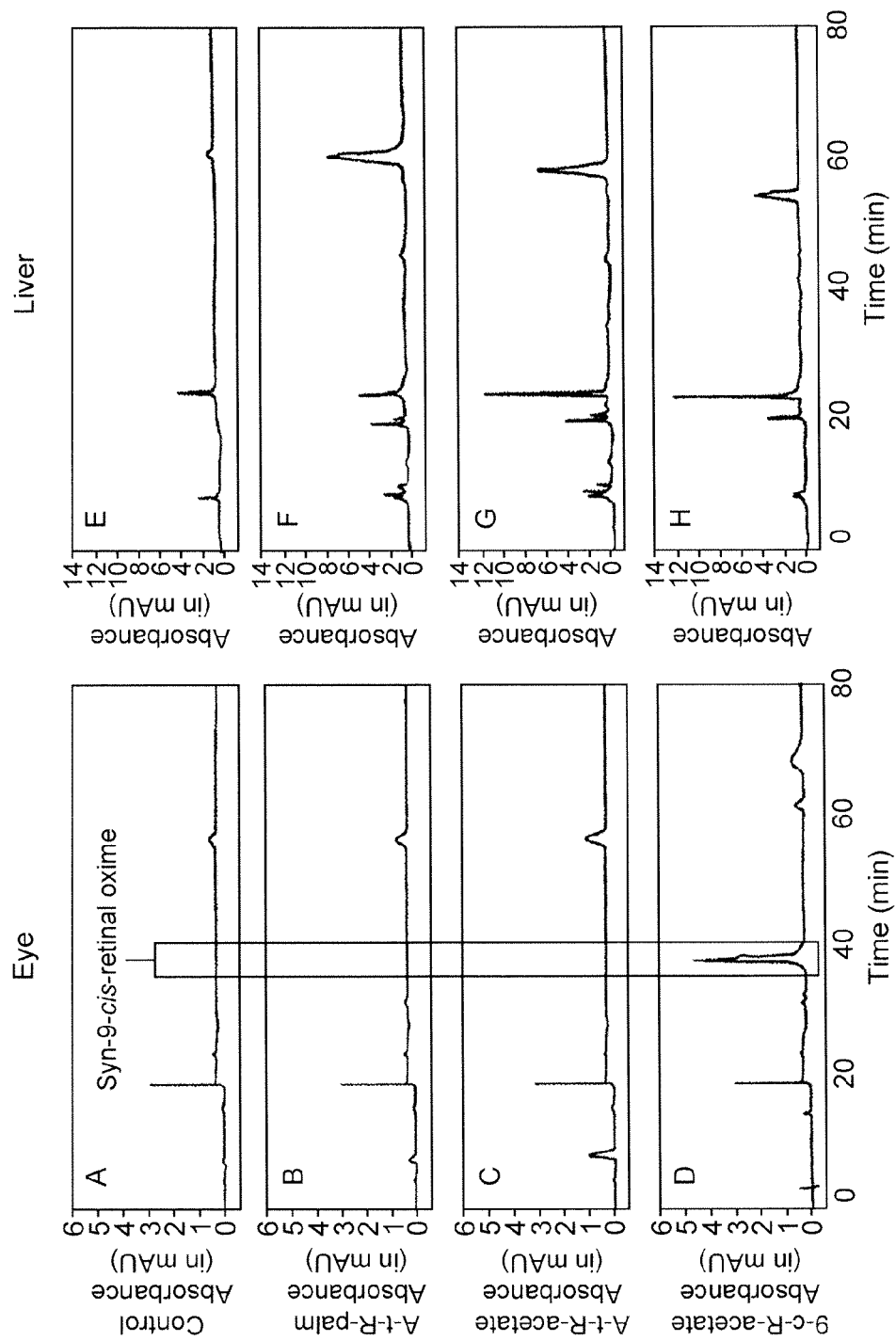
FIG. 1. HPLC chromatogram showing retinoid elution in treated and control mice eye and liver tissue. A. Eyes from dark adapted LRAT−/− mouse. B. Eyes from dark-adapted LRAT−/− mouse gavaged with 5 mg all-trans-retinyl palmitate 2 days prior. C. Eyes from dark-adapted LRAT−/− mouse gavaged with 5 mg all-trans-retinyl acetate 2 days prior. D. Eyes from dark-adapted LRAT−/− mouse gavaged with 6.5 mg 9-cis-retinyl acetate 3 days prior. E. Liver tissue from dark adapted LRAT−/− mouse. F. Liver tissue from dark-adapted LRAT−/− mouse gavaged with 5 mg all-trans-retinyl palmitate 2 days prior. G. Liver tissue from dark-adapted LRAT−/− mouse gavaged with 5 mg all-trans-retinyl acetate 2 days prior. H. Liver tissue from dark-adapted LRAT−/− mouse gavaged with 6.5 mg 9-cis-retinyl acetate 3 days prior.

The present invention provides synthetical retinal derivatives and methods of using such derivatives to restore or stabilize photoreceptor function in a vertebrate visual system. The synthetic retinal derivative is a derivative of 9-cis-retinal or 11-cis-retinal in which the aldehydic group in the polyene chain is modified. The synthetic retinal derivative can be converted directly or indirectly into a retinal or a synthetic retinal analog. Thus, in some aspects, the compounds according to the present invention can be described as a pro-drug, which upon metabolic transformation is converted into 9-cis-retinal, 11-cis-retinal or a synthetic retinal analog thereof. Metabolic transformation can occur, for example by acid hydrolysis, esterase activity, acetyltransferase activity, dehydrogenase activity, or the like.

The synthetic retinal derivative can be a retinoid replacement, supplementing the levels of endogenous retinoid. In some embodiments, the synthetic retinal can bind to opsin, and function as an opsin agonist. As used herein, the term "agonist" refers to a synthetic retinal that binds to opsin and facilitates the ability of an opsin/synthetic retinal complex to respond to light. As an opsin agonist, a synthetic retinal can spare the requirement for endogenous retinoid (e.g., 11-cis-retinal). A synthetic retinal also can restore or improve function (e.g., photoreception) to opsin by binding to opsin and forming a functional opsin/synthetic retinal complex, whereby the opsin/synthetic retinal complex can respond to photons when part of a rod or cone membrane.

Synthetic retinal derivatives can be administered to restore or stabilize photoreceptor function, and/or to ameliorate the effects of a deficiency in retinoid levels. Photoreceptor function can be restored or stabilized, for example, by providing a synthetic retinal derivative as an 11-cis-retinoid replacement and/or an opsin agonist. The synthetic retinal derivative also can ameliorate the effects of a retinoid deficiency on a vertebrate visual system. The synthetic retinal derivative can be administered prophylactically or therapeutically to a vertebrate. Suitable vertebrates include, for example, human and non-human vertebrates. Suitable non-human vertebrates include, for example, mammals, such as dogs (canine), cats (feline), horses (equine) and other domesticated animals.

In one aspect, synthetic retinal derivatives are provided. The synthetic retinal derivatives are derivatives of 9-cis-retinal or 11-cis-retinal in which the aldehydic group in the polyene chain is converted to an ester, ether, alcohol, hemiacetal, acetal, oxime, as further described herein. Such synthetic retinal derivatives include 9-cis-retinyl esters, 9-cis-retinyl ethers, 9-cis-retinol, 9-cis-retinal oximes, 9-cis-retinyl acetals, 9-cis-retinyl hemiacetals, 11-cis-retinyl esters, 11-cis-retinyl ethers, 11-cis-retinol, 11-cis-retinyl oximes, 11-cis-retinyl acetals and 11-cis-retinyl hemiacetals, as further described herein. The synthetic retinal derivative can be metabolized to release a natural or synthetic retinal, such as for example, 9-cis-retinal, 11-cis-retinal or a synthetic retinal analog thereof, such as those described herein or in co-pending International Application No. PCT/US04/07937, filed Mar. 15, 2004, (the disclosure of which is incorporated by reference herein).

In one aspect, the synthetic retinal derivative is a retinyl ester. In some embodiments, the retinyl ester is a 9-cis-retinyl ester or an 11-cis-retinyl ester having a. The ester substituent can be, for example, a carboxylic acid, such as a mono- or polycarboxylic acid. As used herein, a "polycarboxylic acid" is a di-, tri- or higher order carboxylic acid. In some embodiments, the carboxylic acid is a $C_1$-$C_{22}$, $C_2$-$C_{22}$, $C_3$-$C_{22}$, $C_1$-$C_{10}$, $C_2$-$C_{10}$, $C_3$-$C_{10}$, $C_4$-$C_{10}$, $C_4$-$C_8$, $C_4$-$C_6$ or $C_4$ monocarboxylic acid, or polycarboxylic acid.

Suitable carboxylic acid groups include, for example, acetic acid, propionic acid, butyric acid, valeric acid, caproic acid, caprylic acid, pelargonic acid, capric acid, lauric acid, oleic acid, stearic acid, palmitic acid, myristic acid or linoleic acid. The carboxylic acid also can be, for example, oxalic acid (ethanedioic acid), malonic acid (propanedioic acid), succinic acid (butanedioic), fumaric acid (butenedioic acid), malic acid (2-hydroxybutenedioic acid), glutaric acid (pentanedioic acid), adipic acid (hexanedioic acid), pimelic acid (heptanedioic), suberic acid (octanedioic), azelaic acid (nonanedioic acid), sebacic acid (decanedioic acid), citric acid, oxaloacetic acid, ketoglutaratic acid, or the like.

In an exemplary embodiment, the retinyl ester is a 9-cis-retinyl ester or an 11-cis-retinyl ester including a $C_3$-$C_{10}$ polycarboxylic acid substituent. (In this context, the terms "substituent" or "group" refer to a radical covalently linked to the terminal oxygen in the polyene chain.) In another exemplary embodiment, the retinyl ester is a 9-cis-retinyl ester or an 11-cis-retinyl ester including a $C_2$-$C_{22}$ or $C_3$-$C_{22}$ polycarboxylic acid substituent. The polycarboxylic acid substituent can be, for example, succinate, citrate, ketoglutarate, fumarate, malate or oxaloacetate. In another exemplary embodiment, the retinyl ester is a 9-cis-retinyl ester or an 11-cis-retinyl ester including a $C_3$-$C_{22}$ di-carboxylic acid (di-acid) substituent. In some embodiments, the polycarboxylic acid is not 9-cis-retinyl tartarate or 11-cis-retinyl tartarate. In some embodiments, the retinyl ester is not a naturally occurring retinyl ester normally found in the eye. In some embodiments, the retinyl ester is an isolated retinyl ester. As used herein, "isolated" refers to a molecule that exists apart from its native environment and is therefore not a product of nature. An isolated molecule may exist in a purified form or may exist in a non-native environment.

In another aspect, the retinal derivative can be a 9-cis-retinyl ester or ether of the following formula I:

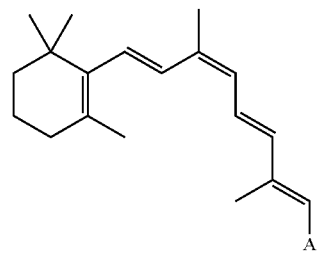

(I)

In some embodiments, A is $CH_2OR$, where R can be an aldehydic group, to form a retinyl ester. A suitable aldehydic group is a $C_1$ to $C_{24}$ straight chain or branched aldehydic group. The aldehydic group also can be a $C_1$ to $C_{14}$ straight chain or branched aldehydic group. The aldehydic group can be a $C_1$ to $C_{12}$ straight chain or branched aldehydic group, such as, for example, acetaldehyde, propionaldehyde, butyraldehyde, valeraldehyde, hexanal, heptanal, octanal, nonanal, decanal, undecanal, dodecanal. R can be a $C_1$ to $C_{10}$ straight chain or branched aldehydic group, a $C_1$ to $C_8$ straight chain or branched aldehydic group or a $C_1$ to $C_6$ straight chain or branched aldehydic group.

R further can be a carboxylate group of a dicarboxylic acid or other carboxylic acid (e.g., a hydroxyl acid) to form a retinyl ester (some of which are also referred to as retinoyl esters). The carboxylic acid can be, for example, oxalic acid (ethanedioic acid), malonic acid (propanedioic acid), succinic acid (butanedioic), fumaric acid (butenedioic acid), malic acid (2-hydroxybutenedioic acid), glutaric acid (pentanedioic acid), adipic acid (hexanedioic acid), pimelic acid (heptanedioic), suberic acid (octanedioic), azelaic acid (nonanedioic acid), sebacic acid (decanedioic acid), citric acid, oxaloacetic acid, ketoglutaratic acid, or the like.

R can also be an alkane group, to form a retinyl alkane ether. Suitable alkane groups include, for example, $C_1$ to $C_{24}$ straight chain or branched alkyls, such as, for example, methane, ethane, butane, isobutane, pentane, isopentane, hexane, heptane, octane or the like. For example, the alkane group can be a linear, iso-, sec-, tert- or other branched lower alkyl ranging from $C_1$ to $C_6$. The alkane group also can be a linear, iso-, sec-, tert- or other branched medium chain length alkyl ranging from $C_8$ to $C_{14}$. The alkane group also can be a linear, iso-, sec-, tert- or other branched long chain length alkyl ranging from $C_{16}$ to $C_{24}$.

R further can be an alcohol group, to form a retinyl alcohol ether. Suitable alcohol groups can be linear, iso-, sec-, tert- or other branched lower alcohols ranging from $C_1$ to $C_6$, linear, iso-, sec-, tert- or other branched medium chain length alcohols ranging from $C_8$ to $C_{14}$, or linear, iso-, sec-, tert- or other branched long chain length alkyl ranging from $C_{16}$ to $C_{24}$. The alcohol group can be, for example, methanol, ethanol, butanol, isobutanol, pentanol, hexanol, heptanol, octanol, or the like R also can be a carboxylic acid, to form a retinyl carboxylic acid ether. Suitable alcohol groups can be linear, iso-, sec-, tert- or other branched lower carboxylic acids ranging from $C_1$ to $C_6$, linear, iso-, sec-, tert- or other branched medium chain length carboxylic acids ranging from $C_8$ to $C_{14}$, or linear, iso-, sec-, tert- or other branched long chain length carboxylic acids ranging from $C_{16}$ to $C_{24}$. Suitable carboxylic acid groups include, for example, acetic acid, propionic acid, butyric acid, valeric acid, caproic acid, caprylic acid, pelargonic acid, capric acid, lauric acid, oleic acid, stearic acid, palmitic acid, myristic acid, linoleic acid, succinic acid, fumaric acid or the like.

The retinyl derivative can be a retinyl hemiacetal, where A is CH(OH)OR. R can be any of the R groups set forth above in Formula I. R is typically a lower alkane, such as a methyl or ethyl group, or a $C_1$ to $C_7$ saturated and unsaturated, cyclic or acyclic alkane, with or without hetero atoms, as described herein.

The retinyl derivative can be a retinyl acetal, where A is $CH(OR_a)OR_b$. Each of $R_a$ and $R_b$ can be independently selected from any of the R groups set forth above in Formula I. $R_a$ and $R_b$ are typically a $C_1$ to $C_7$ saturated and unsaturated, cyclic or acyclic alkane, with or without hetero atoms, as described herein.

The retinyl derivative also can be a retinyl oxime, where A is CH:NOH or CH:NOR. R can be any of the R groups set forth above in Formula I. R is typically a hydrogen, or an alkane.

Examples of suitable synthetic retinal derivatives include, for example, 9-cis-retinyl acetate, 9-cis-retinyl formate, 9-cis-retinyl succinate, 9-cis-retinyl citrate, 9-cis-retinyl ketoglutarate, 9-cis-retinyl fumarate, 9-cis-retinyl malate, 9-cis-retinyl oxaloacetate, 9-cis-retinal oxime, 9-cis-retinal O-methyl oximes, 9-cis-retinal O-ethyl oximes, and 9-cis-retinal methyl acetals and hemi acetals, 9-cis-retinyl methyl ether, 9-cis-retinyl ethyl ether, and 9-cis-retinyl phenyl ether.

In a related aspect, the retinal derivative can be an 11-cis-retinyl ester or ether of the following formula II:

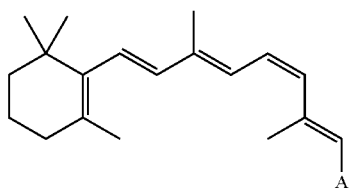

(II)

A can be any of the groups set forth above in Formula I.

Examples of suitable synthetic retinal derivatives include, for example, 11-cis-retinyl acetate, 11-cis-retinyl formate, 11-cis-retinyl succinate, 11-cis-retinyl citrate, 11-cis-retinyl ketoglutarate, 11-cis-retinyl fumarate, 11-cis-retinyl malate, 11-cis-retinal oxime, 11-cis-retinal O-methyl oxime, 11-cis-retinal O-ethyl oximes and 11-cis-retinal methyl acetals and hemi acetals, 11-cis-retinyl methyl ether, 11-cis-retinyl ethyl ether.

In additional aspects, the synthetic retinal derivatives can be, for example, a derivative of a 9-cis-retinyl ester, a 9-cis-retinyl ether, an 11-cis-retinyl ester or an 11-cis-retinyl ethers such as, for example, an acyclic retinyl ester or ethers, a retinyl ester or ether with a modified polyene chain length, such as a trienoic or tetraenoic retinyl ester or ether; a retinyl ester or ether with a substituted polyene chain, such as alkyl, halogen or heteratom-substituted polyene chains; a retinyl ester or ether with a modified polyene chain, such as a trans- or cis-locked polyene chain, or with, for example, allene or alkyne modifications; and a retinyl ester or ether with a ring modification(s), such as heterocyclic, heteroaromatic or substituted cycloalkane or cycloalkene rings.

The synthetic retinal derivative can be a retinyl ester or ether of the following formula III:

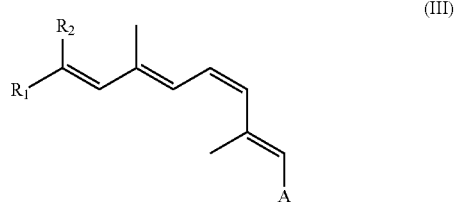

(III)

A can be any of the groups set forth above for formula (I). $R_1$ and $R_2$ can be independently selected from linear, iso-, sec-, tert- and other branched alkyl groups as well as substituted alkyl groups, substituted branched alkyl, hydroxyl, hydroalkyl, amine, amid; or the like. $R_1$ and $R_2$ can independently be lower alkyl, which means straight or branched alkyl with 1-6 carbon atom(s) such as methyl, ethyl, propyl, isopropyl, butyl, isobutyl, tert-butyl, pentyl, hexyl, or the like. Suitable substituted alkyls and substituted branch alkyls include, for example, alkyls, branched alkyls and cyclo-alkyls substituted with oxygen, hydroxyl, nitrogen, amide, amine, halogen, heteroatom or other groups. Suitable heteroatoms include, for example, sulfur, silicon, and fluoro- or bromo-substitutions.

$R_1$ or $R_2$ also can be a cyclo-alkyl such as, for example, hexane, cyclohexane, benzene as well as a substituted cyclo-alkyl. Suitable substituted cyclo-alkyls include, for example, cyclo-alkyls substituted with oxygen, hydroxyl, nitrogen, amide, amine, halogen, heteroatom and/or other groups. Suitable heteroatoms include, for example, sulfur, silicon, and fluoro- or bromo-substitutions.

The synthetic retinal derivative also can have a modified polyene chain length, such as the following formula IV:

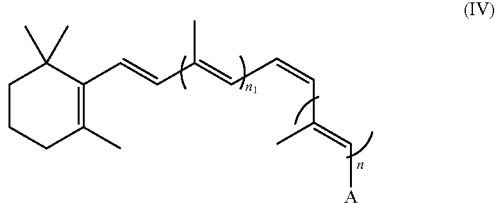

(IV)

A can be any of the groups set forth above for formula (I). The polyene chain length can be extended by 1, 2, or 3 alkyl, alkene or alkylene groups. According to formula (IV), each n and $n_1$ can be independently selected from 1, 2, or 3 alkyl, alkene or alkylene groups, with the proviso that the sum of the n and $n_1$ is at least 1.

The synthetic retinal derivative also can have a substituted polyene chain of the following formula V:

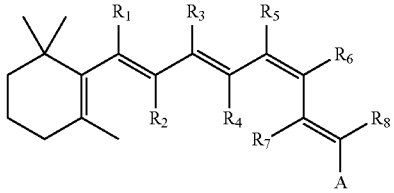

(V)

A can be any of the groups set forth above for formula (I). Each of $R_1$ to $R_8$ can be independently selected from hydrogen, alkyl, branched alkyl, cyclo-alkyl, halogen, a heteratom, or the like. Suitable alkyls include, for example, methyl, ethyl, propyl, substituted alkyl (e.g., alkyl with hydroxyl, hydroalkyl, amine, amide) or the like. Suitable branched alkyls can be, for example, isopropyl, isobutyl, substituted branched alkyl, or the like. Suitable cyclo-alkyls can include, for example, cyclohexane, cycloheptane, and other cyclic alkanes as well as substituted cyclic alkanes such as substituted cyclohexane or substituted cycloheptane. Suitable halogens include, for example, bromine, chlorine, fluorine, or the like. Suitable heteroatoms include, for example, sulfur, silicon, and fluoro- or bromo-substitutions. Suitable substituted alkyls, substituted branch alkyls and substituted cyclo-alkyls include, for example, alkyls, branched alkyls and cyclo-alkyls substituted with oxygen, hydroxyl, nitrogen, amide, amine, halogen, heteroatom or other groups.

For example, the synthetic retinal derivative can be selected from the following: a 9-ethyl-11-cis-retinyl ester, ether, oxime, acetal or hemiacetal; a 7-methyl-11-cis-retinyl ester, ether, oxime, acetal or hemiacetal; a 13-desmethyl-11-cis-retinyl ester, ether, oxime, acetal or hemiacetal; an 11-cis-10-F-retinyl ester, ether, oxime, acetal or hemiacetal; an 11-cis-10-Cl-retinyl ester, ether, oxime, acetal or hemiacetal; an 11-cis-10-methyl-retinyl ester, ether, oxime, acetal or hemiacetal; an 11-cis-10-ethyl-retinyl ester, ether, oxime, acetal or hemiacetal; a 9-cis-10-F-retinyl ester, ether, oxime, acetal or hemiacetal; a 9-cis-10-Cl-retinyl ester, ether, oxime, acetal or hemiacetal; a 9-cis-10-methyl-retinyl ester, ether, oxime, acetal or hemiacetal; a 9-cis-10-ethyl-retinyl ester, ether, oxime, acetal or hemiacetal; an 11-cis-12-F-retinyl ester, ether, oxime, acetal or hemiacetal; an 11-cis-12-Cl-retinyl ester, ether, oxime, acetal or hemiacetal; an 11-cis-12-methyl-retinyl ester, ether, oxime, acetal or hemiacetal; an 11-cis-10-ethyl-retinyl ester, ether, oxime, acetal or hemiacetal; a 9-cis-12-F-retinyl ester, ether, oxime, acetal or hemiacetal; a 9-cis-12-Cl-retinyl ester, ether, oxime, acetal or hemiacetal; a 9-cis-12-methyl-retinyl ester, ether, oxime, acetal or hemiacetal; an 11-cis-14-F-retinyl ester, ether, oxime, acetal or hemiacetal; an 11-cis-14-methyl-retinyl ester, ether, oxime, acetal or hemiacetal; an 11-cis-14-ethyl-retinyl ester, ether, oxime, acetal or hemiacetal; a 9-cis-14-F-retinyl ester, ether, oxime, acetal or hemiacetal; a 9-cis-14-methyl-retinyl ester, ether, oxime, acetal or hemiacetal; a 9-cis-14-ethyl-retinyl ester, ether, oxime, acetal or hemiacetal; or the like.

The synthetic retinal derivative further can have a modified ring structure. Suitable examples include, for example, derivatives containing ring modifications, aromatic analogs and heteroaromatic analogs of the following formulae VI, VII and VIII, respectively:

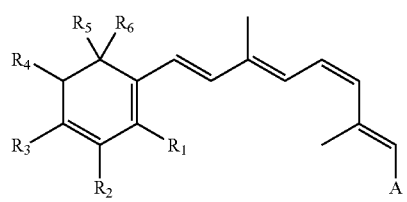

(VI)

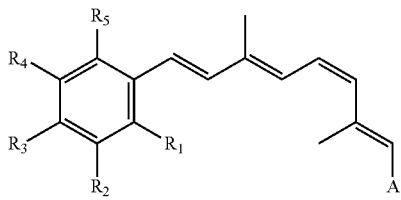

(VII)

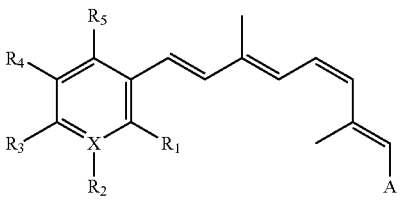

(VIII)

A can be any of the groups set forth above for formula (I). Each of $R_1$ to $R_6$, as applicable, can be independently selected from hydrogen, alkyl, substituted alkyl, hydroxyl, hydroalkyl, amine, amide, halogen, a heteratom, or the like. Suitable alkyls include, for example, methyl, ethyl, propyl, isopropyl, butyl, isobutyl or the like. Suitable halogens include, for example, bromine, chlorine, fluorine, or the like. Suitable heteroatoms include, for example, sulfur, silicon, or nitrogen. In formulae VII, X can be, for example, sulfur, silicon, nitrogen, fluoro- or bromo-substitutions. Similarly, 9-cis-synthetic retinal derivatives containing ring modifications, aromatic analogs and heteroaromatic analogs of those shown in formulae VI, VII and VIII are contemplated.

The synthetic retinal derivative also can have a modified polyene chain. Suitable derivatives include, for example, those with a trans/cis locked configuration, 6s-locked analogs, as well as modified allene, alkene, alkyne or alkylene groups in the polyene chain. In one example, the derivative is an 11-cis-locked analog of the following formula IX:

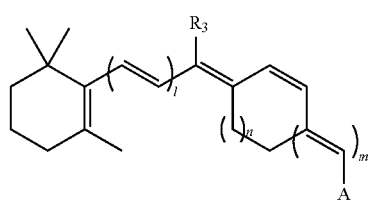

(IX)

A can be any of the groups set forth above for formula (I). $R_3$ can be, for example, hydrogen, methyl or other lower alkane or branch alkane. n can be 0 to 4. m plus 1 equals 1, 2 or 3.

In one embodiment, the synthetic retinal derivative can be an 11-cis-locked analog of the following formula X:

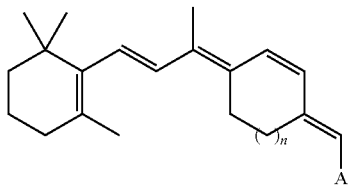

(X)

n can be 1 to 4. A can be any of the groups set forth above for formula (I).

The synthetic retinal derivative is a 9,11,13-tri-cis-7-ring retinyl ester or ether, an 11,13-di-cis-7-ring retinyl ester or ether, an 11-cis-7-ring retinyl ester or ether or a 9,11-di-cis-7-ring retinyl ester or ether.

In another example, the synthetic retinal derivative is a 6s-locked analog of formula XI. A can be any of the groups set forth above for formula (I). $R_1$ and $R_2$ can be independently selected from hydrogen, methyl and other lower alkyl and substituted lower alkyl. $R_3$ can be independently selected from an alkene group at either of the indicated positions.

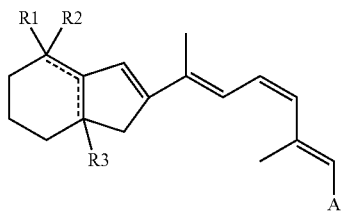

(XI)

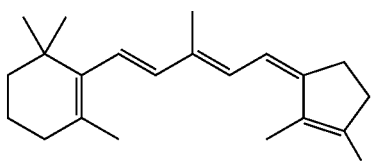

(XII)

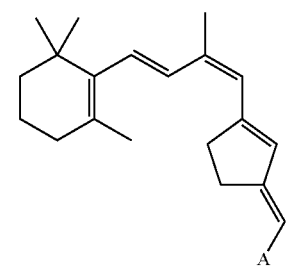

(XIII)

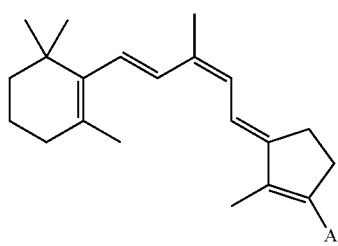

(XIV)

The synthetic retinal derivative can be a 9-cis-ring-fused derivative, such as, for example, those shown in formulae XII-XIV. A can be any of the groups set forth above for formula (I).

The synthetic retinal derivative also can be of the following formula XV or XVI.

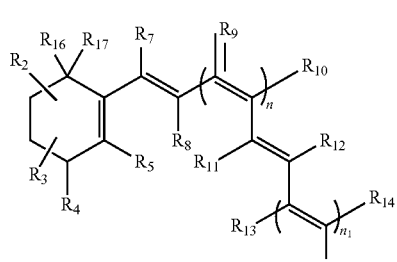

(XV)

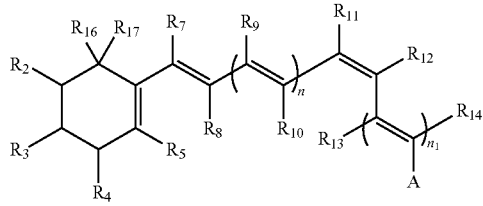

(XVI)

A can be any of the groups set forth above for formula (I). Each of $R_2$ to $R_5$, $R_7$ to $R_{14}$, $R_{16}$ and $R_{17}$ can be absent or independently selected from hydrogen, alkyl, branched alkyl, halogen, hydroxyl, hydroalkyl, amine, amide, a heteratom, or the like. Suitable alkyls include, for example, methyl, ethyl, propyl, substituted alkyl (e.g., alkyl with hydroxyl, hydroalkyl, amine, amide), or the like. Suitable branched alkyl can be, for example, isopropyl, isobutyl, substituted branched alkyl, or the like. Suitable halogens include, for example, bromine, chlorine, fluorine, or the like. Suitable heteroatoms include, for example, sulfur, silicon, and fluoro- or bromo-substitutions. Suitable substituted alkyls and substituted branch alkyls include, for example, alkyls and branched alkyls substituted with oxygen, hydroxyl, nitrogen, amide, amine, halogen, heteroatom or other groups. Each of n and $n_1$ can be independently selected from 1, 2, or 3 alkyl, alkene or alkylene groups, with the proviso that the sum of the n and $n_1$ is at least 1. In addition, $R_3$-$R_4$ and/or $R_2$-$R_{16}$ can comprise an alkene group in the cyclic carbon ring, in which case $R_{17}$ is absent. $R_{10}$ and $R_{13}$ together can form a cyclo-alkyl, such as a five, six, seven or eight member cyclo-alkyl or substituted cyclo-alkyl, such as, for example, those shown in Formulae IX, X, XII, XIII and XIV.

Methods of making synthetic retinals and derivatives are disclosed in, for example, the following references: *Anal. Biochem.* 272:232-42 (1999); *Angew. Chem.* 36:2089-93 (1997); *Biochemistry* 14:3933-41 (1975); *Biochemistry* 21:384-93 (1982); *Biochemistry* 28:2732-39 (1989); *Biochemistry* 33:408-16 (1994); *Biochemistry* 35:6257-62 (1996); *Bioorganic Chemistry* 27:372-82 (1999); *Biophys. Chem.* 56:31-39 (1995); *Biophys. J.* 56:1259-65 (1989); *Biophys. J.* 83:3460-69 (2002); *Chemistry* 7:4198-204 (2001); *Chemistry* (Europe) 5:1172-75 (1999); *FEBS* 158:1 (1983); *J. Am. Chem. Soc.* 104:3214-16 (1982); *J. Am. Chem. Soc.* 108:6077-78 (1986); *J. Am. Chem. Soc.* 109:6163 (1987); *J. Am. Chem. Soc.* 112:7779-82 (1990); *J. Am. Chem. Soc.* 119:5758-59 (1997); *J. Am. Chem. Soc.* 121:5803-04 (1999); *J. American Chem. Soc.* 123:10024-29 (2001); *J. American*

Chem. Soc. 124:7294-302 (2002); J. Biol. Chem. 276:26148-53 (2001); J. Biol. Chem. 277:42315-24 (2004); J. Chem. Soc.-Perkin T. 1:1773-77 (1997); J. Chem. Soc.-Perkin T. 1:2430-39 (2001); J. Org. Chem. 49:649-52 (1984); J. Org. Chem. 58:3533-37 (1993); J. Physical Chemistry B 102:2787-806 (1998); Lipids 8:558-65; Photochem. Photobiol. 13:259-83 (1986); Photochem. Photobiol. 44:803-07 (1986); Photochem. Photobiol. 54:969-76 (1991); Photochem. Photobiol. 60:64-68 (1994); Photochem. Photobiol. 65:1047-55 (1991); Photochem. Photobiol. 70:111-15 (2002); Photochem. Photobiol. 76:606-615 (2002); Proc. Natl Acad. Sci. USA 88:9412-16 (1991); Proc. Natl Acad. Sci. USA 90:4072-76 (1993); Proc. Natl Acad. Sci. USA 94:13442-47 (1997); and Proc. R. Soc. Lond. Series B. Biol. Sci. 233(1270): 55-76 1988) (the disclosures of which are incorporated by reference herein).

Retinyl esters can be formed by methods known in the art such as, for example, by acid-catalyzed esterification of a retinol with a carboxylic acid, by reaction of an acyl halide with a retinol, by transesterification of a retinyl ester with a carboxylic acid, by reaction of a primary halide with a carboxylate salt of a retinoic acid, by acid-catalyzed reaction of an anhydride with a retinal, or the like. In an example, retinyl esters can be formed by acid-catalyzed esterification of a retinal with a carboxylic acid, such as, acetic acid, propionic acid, butyric acid, valeric acid, caproic acid, caprylic acid, pelargonic acid, capric acid, lauric acid, oleic acid, stearatic acid, palmitic acid, myristic acid, linoleic acid, succinic acid, fumaric acid or the like. In another example, retinyl esters can be formed by reaction of an acyl halide with a retinol (see, e.g., Van Hooser et al., Proc. Natl. Acad. Sci. USA, 97:8623-28 (2000)). Suitable acyl halides include, for example, acetyl chloride, palmitoyl chloride, or the like.

Retinyl ethers can be formed by methods known in the art, such as for example, reaction of a retinol with a primary alkyl halide.

Trans-retinoids can be isomerized to cis-retinoids by exposure to UV light. For example, all-trans-retinal, all-trans-retinol, all-trans-retinyl ester or all-trans-retinoic acid can be isomerized to 9-cis-retinal, 9-cis-retinol, 9-cis-retinyl ester or 9-cis-retinoic acid, respectively. trans-Retinoids can be isomerized to 9-cis-retinoids by, for example, exposure to a UV light having a wavelength of about 365 nm, and substantially free of shorter wavelengths that cause degradation of cis-retinoids, as further described herein.

Retinyl acetals and hemiacetals can be prepared, for example, by treatment of 9-cis- and 11-cis-retinals with alcohols in the presence of acid catalysts. Water formed during reaction is removed, for example by $Al_2O_3$ of a molecular sieve.

Retinyl oximes can be prepared, for example, by reaction of a retinal with hydroxylamine, O-methyl- or O-ethylhydroxylamine, or the like.

For a specific opsin protein, a suitable synthetic retinal derivatives can be identified, for example, by an expression system expressing the opsin protein. Suitable animal models include, for example, RPE65–/– or LRAT –/– mice (see, e.g., Van Hooser et al., J. Biol. Chem. 277:19173-82 (2002); Baehr et al., Vision Res. 43:2957-58 (2003); Batten et al., J. Biol. Chem. 279:10422-32 (2004); Kuksa et al., Vision Res. 43:2959-81 (2003); Thompson et al., Dev. Ophthalmol. 37:141-54 (2003)). Other suitable non-human animal models further include other mouse, rat or primate systems. Such animal models can be prepared, for example, by promoting homologous recombination between a nucleic acid encoding an opsin in its chromosome and an exogenous nucleic acid encoding a mutant opsin. In one aspect, homologous recombination is carried out by transforming embryo-derived stem (ES) cells with a vector containing an opsin gene, such that homologous recombination occurs, followed by injecting the ES cells into a blastocyst, and implanting the blastocyst into a foster mother, followed by the birth of the chimeric animal (see, e.g., Capecchi, Science 244:1288-92 (1989)). The chimeric animal can be bred to produce additional transgenic animals.

Suitable expression systems also can include, for example, in vitro or in vivo systems. Suitable in vitro systems include for example, coupled transcription-translation systems. Suitable in vivo systems include, for example, cells expressing an opsin protein. For example, cells of a vertebrate visual system can be adapted for culture in vitro, or recombinant cell lines expressing an opsin protein can be used. The cell lines are typically stable cell lines expressing the opsin protein. A synthetic retinal or synthetic retinal derivative can be added to the cell culture media, and the cells cultured for a suitable period of time to allow the production of opsin/rhodopsin. Opsin and/or rhodopsin can be isolated (e.g., by immunoaffinity). Isolated protein samples are examined to determine the amount of pigment formed, and absorbance maxima. Methods of introducing nucleic acids into vertebrate cells are disclosed in, for example, Sambrook et al., Molecular Cloning: A Laboratory Manual, Cold Spring Harbor Laboratory Press (Cold Spring Harbor, N.Y., 2001).

Recombinant cell lines expressing opsin protein can be prepared by, for example, introducing an expression construct encoding an opsin protein into a suitable cell line. The expression construct typically includes a promoter operably linked to a nucleic acid encoding an opsin protein, and optionally a termination signal(s). Nucleic acids encoding opsin can be obtained, for example, by using information from a database (e.g., a genomic or cDNA library), by polymerase chain reaction, or die like. For example opsin-encoding nucleic acids can be obtained by hybridization, (See generally Sambrook et al. (supra).) An opsin encoding nucleic acid can be obtained by hybridization under conditions of low, medium or high stringency.

Opsin-encoding nucleic acids can be obtained under conditions of high stringency hybridization. By way of example, and not limitation, procedures using conditions of high stringency are as follows: Prehybridization of filters containing DNA is carried out for 8 hours to overnight 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in prehybridization mixture containing 100 denatured salmon sperm DNA and 5-20×10$^6$ cpm of $^{32}$P-labeled probe. Washing of filters is done at 65° C. for 1 hour in a solution containing 2×SSC, 0.01% PVP, 0.01% Ficoll, and 0.01% BSA. This is followed by a wash in 0.1×SSC at 50° C. for 45 minutes before autoradiography. Other conditions of high stringency which can be used are well known in the art. (See generally Sambrook et al. (supra).)

The expression construct can optionally include one or more origins of replication and/or selectable marker(s) (e.g., an antibiotic resistance gene). Suitable selectable markers include, for example, those conferring resistance to ampicillin, tetracycline, neomycin, G418, and the like. Suitable cell lines include, for example, HEK293 cells, T-REx™-293 cells, CHO cells and other cells or cell lines.

The UV-visible spectra of rhodopsin (comprising opsin and a synthetic retinal) can be monitored to determine whether the synthetic retinal has formed a Schiff's base with the opsin protein. For example, acid-denatured, purified protein can be analyzed to determine whether an absorbance maxima of approximately 490 nm is present, providing evidence that the synthetic retinal derivative forms a Schiff's base with the opsin protein. Hydroxylamine treatment can be used to confirm the Schiff's base is sequestered from the external environment.

Suitable synthetic retinal derivatives also can be selected by molecular modeling of rhodopsin. The coordinates for rhodopsin crystal structure are available from the Protein Data Bank (1 HZX) (Teller et al., *Biochemistry* 40:7761-72 (2001)). The effects of amino acid substitutions on the structure of rhodopsin, and on the contacts between opsin and 11-cis-retinal, or a synthetic retinal, can be determined by molecular modeling.

The coordinates for the rhodopsin crystal structure from the Protein Data Bank (1 HZX) (Teller et al., *Biochemistry* 40:7761-72 (2001)) can be used to generate a computer model. The addition of hydrogen atoms and optimization can be done, for example, using Insight II (InsightII release 2000, Accelrys, Inc., San Diego, Calif.). Crystallographic water can be removed, and water molecules introduced based on the accessible space in the extracellular region. Typically, no minimization is performed before water is added. A water layer (e.g., 5 Å thick) can be used to coat the extracellular part of rhodopsin as well as residues in contact with polar phospholipids heads. All of the water molecules can be allowed to move freely, as is the extracellular half of rhodopsin, with retinal. If no water cap is put on the cytoplasmic part of rhodopsin, this part of the molecule can be frozen to prevent degradation of the model.

A water cap can be put on the extracellular part of rhodopsin (together with that part buried in membrane in contact with polar heads of phospholipids). Water and the extracellular part of rhodopsin can be allowed to move and the movement modeled at any suitable frequency. For example, the movement of the modeled rhodopsin can be modeling at 100 ps simulations.

Synthetic retinals can be contacted with an opsin protein under conditions suitable and for a period of time sufficient for the formation of an opsin protein/synthetic retinal complex. The stability of the opsin/synthetic retinal complex can be determined by methods described herein or as known to the skilled artisan. The opsin in the opsin/synthetic retinal complex is stabilized when it exhibits increased stability (e.g., increased half-life when bound to the synthetic retinal as compared with free opsin not bound to retinoid), is less sensitive to hydroxylamine, exhibits less accumulation in aggresomes, or the like).

The synthetic retinal can be contacted with the opsin protein in vitro or in vivo. For example, the opsin protein can be synthesized in an in vitro translation system (e.g., a wheat germ or reticulocyte lysate expression system) and the synthetic retinal added to the expression system. The opsin protein can be contacted with the opsin protein ex vivo, and then the complex can be administered to a vertebrate eye.

In another aspect, methods of using a synthetic retinal derivative are provided to restore or stabilize photoreceptor function, or to ameliorate photoreceptor loss, in a vertebrate visual system. A synthetic retinal derivative can be administered to a vertebrate eye(s) having a retinoid deficiency (e.g., a deficiency of 11-cis-retinal), an excess of free opsin, an excess of retinoid waste (e.g., degradation) products or intermediates in the recycling of all-trans-retinal, or the like. The vertebrate eye typically comprises a wildtype opsin protein. Methods of determining endogenous retinoid levels in a vertebrate eye, and a deficiency of such retinoids, are disclosed in, for example, U.S. Provisional Patent Application No. 60/538,051 (filed Feb. 12, 2004) (the disclosure of which is incorporated by reference herein). Other methods of determining endogenous retinoid levels in a vertebrate eye, and a deficiency of such retinoids, include for example, analysis by high pressure liquid chromatography (HPLC) of retinoids in a sample from a subject. For example, retinoid levels or a deficiency in such levels can be determined from a blood sample from a subject.

A blood sample can be obtained from a subject and retinoid types and levels in the sample can be separated and analyzed by normal phase high pressure liquid chromatography (HPLC) (e.g., with a HP1100 HPLC and a Beckman, Ultrasphere-Si, 4.6 mm×250 mm column using 10% ethyl acetate/90% hexane at a flow rate of 1.4 ml/minute). The retinoids can be detected by, for example, detection at 325 nm using a diode-array detector and HP Chemstation A.03.03 software. A deficiency in retinoids can be determined, for example, by comparison of the profile of retinoids in the sample with a sample from a control subject (e.g., a normal subject).

As used herein, absent, deficient or depleted levels of endogenous retinoid, such as 11-cis-retinal, refer to levels of endogenous retinoid lower than those found in a healthy eye of a vertebrate of the same species. A synthetic retinal derivative can spare the requirement for endogenous retinoid.

As used herein, "prophylactic" and "prophylactically" refer to the administration of a synthetic retinal derivative to prevent deterioration or further deterioration of the vertebrate visual system, as compared with a comparable vertebrate visual system not receiving the synthetic retinal derivative. The term "restore" refers to a long-term (e.g., as measured in weeks or months) improvement in photoreceptor function in a vertebrate visual system, as compared with a comparable vertebrate visual system not receiving the synthetic retinal derivative. The term "stabilize" refers to minimization of additional degradation in a vertebrate visual system, as compared with a comparable vertebrate visual system not receiving the synthetic retinal derivative.

In one aspect, the vertebrate eye is characterized as having Leber Congenital Amaurosis ("LCA"). This disease is a very rare childhood condition that effects children from birth or shortly there after. It affects both rods and cones in the eye. For example, certain mutations in the genes encoding RPE65 and LRAT proteins are involved in LCA. Mutations in both genes result in a person's inability to make 11-cis-retinal in adequate quantities. Thus, 11-cis-retinal is either absent or present in reduced quantities. In RPE65-defective individuals, retinyl esters build up in the RPE. LRAT-defective individuals are unable to make esters and subsequently secrete any excess retinoids. For LCA, a synthetic retinal derivative can be used to replace the absent or depleted 11-cis-retinal.

In another aspect, the vertebrate eye is characterized as having Retinitis Punctata Albesciens. This disease is a form of Retinitis Pigmentosa that exhibits a shortage of 11-cis-retinal in the rods. A synthetic retinal derivative can be used to replace the absent or depleted 11-cis retinal.

In another aspect, the vertebrate eye is characterized as having Congenital Stationary Night Blindness ("CSNB") or Fundus Albipunctatus. This group of diseases is manifested by night blindness, but there is not a progressive loss of vision as in the Retinitis Pigmentosa. Some forms of CSNB are due to a delay in the recycling of 11-cis-retinal. Fundus Albipunctatus until recently was thought to be a special case of CSNB where the retinal appearance is abnormal with hundreds of small white dots appearing in the retina. It has been shown recently that this is also a progressive disease, although with a much slower progression than Retinitis Pigmentosa. It is caused by a gene defect that leads to a delay in the cycling of 11-cis-retinal. Thus, a synthetic retinal derivative(s) can be administered to restore photoreceptor function by retinoid replacement.

In yet another aspect, the vertebrate eye is characterized as having age-related macular degeneration ("AMD"). AMD can be wet or dry forms. In AMD, vision loss occurs when complications late in the disease either cause new blood vessels to grow under the retina or the retina atrophies. Without intending to be bound by any particular theory, excessive production of waste products from the photoreceptors may overload the RPE. This is due to a shortfall of 11-cis-retinal available to bind opsin. Free opsin is not a stable compound and can spontaneously cause firing of the biochemical reactions of the visual cascade without the addition of light.

Administration of a synthetic retinal derivative to the vertebrate eye can reduce the deficiency of 11-cis-retinal and quench spontaneous misfiring of the opsin. Administration of a synthetic retinal derivative can lessen the production of waste products and/or lessen drusen formation, and reduce or slow vision loss (e.g., choroidal neovascularization and/or chorioretinal atrophy).

In yet other aspects, a synthetic retinal derivative is administered to an aging subject, such as a human. As used herein, an aging human subject is typically at least 45, or at least 50, or at least 60, or at least 65 years old. The subject has an aging eye, which is characterized as having a decrease in night vision and/or contrast sensitivity. Excess unbound opsin randomly excites the visual transduction system. This creates noise in the system and thus more light and more contrast are necessary to see well. Quenching these free opsin molecules with a synthetic retinal will reduce spontaneous misfiring and increase the signal to noise ratio, thereby improving night vision and contrast sensitivity.

Synthetic retinal derivatives can be administered to human or other non-human vertebrates. The synthetic retinal derivative can be substantially pure, in that it contains less than about 5% or less than about 1%, or less than about 0.1%, of other retinoids. A combination of synthetic retinal derivatives can be administered.

Synthetic retinal derivatives can be delivered to the eye by any suitable means, including, for example, oral, intravenous, intramuscular or local administration. Modes of local administration can include, for example, eye drops, intraocular injection or periocular injection. Periocular injection typically involves injection of the synthetic retinal derivative into the conjunctiva or to the tennon (the fibrous tissue overlying the eye). Intraocular injection typically involves injection of the synthetic retinal derivative into the vitreous. The administration can be non-invasive, such as by eye drops or oral dosage form.

Synthetic retinal derivatives can be formulated, for example, as pharmaceutical compositions for local administration to the eye and/or for intravenous, intramuscular or oral administration. In some embodiments, the pharmaceutical composition is not a topical formulation. In other embodiments, the pharmaceutical composition is not a cosmetic formulation.

Synthetic retinal derivatives can be formulated for administration using pharmaceutically acceptable vehicles as well as techniques routinely used in the art. A vehicle can be selected according to the solubility of the synthetic retinal derivative. Suitable pharmaceutical compositions include those that are administrable locally to the eye, such as by eye drops, injection or the like. In the case of eye drops, the formulation can also optionally include, for example, ophthalmologically compatible agents such as isotonizing agents such as sodium chloride, concentrated glycerin, and the like; buffering agents such as sodium phosphate, sodium acetate, and the like; surfactants such as polyoxyethylene sorbitan mono-oleate (also referred to as Polysorbate 80), polyoxyl stearate 40, polyoxyethylene hydrogenated castor oil, and the like; stabilization agents such as sodium citrate, sodium edentate, and the like; preservatives such as benzalkonium chloride, parabens, and the like; and other ingredients. Preservatives can be employed, for example, at a level of from about 0.001 to about 1.0% weight/volume. The pH of the formulation is usually within the range acceptable to ophthalmologic formulations, such as within the range of about pH 4 to 8.

Suitable pharmaceutical compositions also include those formulated for injection. For example, We synthetic retinal derivative can be provided in an injection grade saline solution, in the form of an injectable liposome solution, or other carriers or vehicles. Intraocular and periocular injections are known to those skilled in the art and are described in numerous publications including, for example, *Ophthalmic Surgery: Principles of Practice*, Ed., G. L. Spaeth, W. B. Sanders Co., Philadelphia, Pa., U.S.A., pages 85-87 (1990).

A synthetic retinal derivative also can be administered in a time release formulation, for example in a composition which includes a slow release polymer. The synthetic retinal derivative can be prepared with a carrier(s) that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., *Remington "Pharmaceutical Sciences"*, 17 Ed., Gennaro (ed.), Mack Publishing Co., Easton, Pa. (1985).)

The doses of the synthetic retinal derivatives can be suitably selected depending on the clinical status, condition and age of the subject, dosage form and the like. In the case of eye drops, a synthetic retinal derivative can be administered, for example, from about 0.01 mg, about 0.1 mg, or about 1 mg, to about 25 mg, to about 50 mg, or to about 90 mg per single dose. Eye drops can be administered one or more times per day, as needed. In the case of injections, suitable doses can be, for example, about 0.0001 mg, about 0.001 mg, about 0.01 mg, or about 0.1 mg to about 10 mg, to about 25 mg, to about 50 mg, or to about 500 mg of the synthetic retinal derivative, one to four times per week. In other embodiments, about 1.0 to about 300 mg of synthetic retinal derivative can be administered one to three to five times per week.

Oral doses can typically range from about 1.0 to about 1000 mg, one to four times, or more, per day. An exemplary dosing range for oral administration is from about 10 to about 250 mg one to three times per day.

The following examples are provided merely as illustrative of various aspects of the invention and shall not be construed to limit the invention in any way.

EXAMPLES

Example 1

Figure 2:
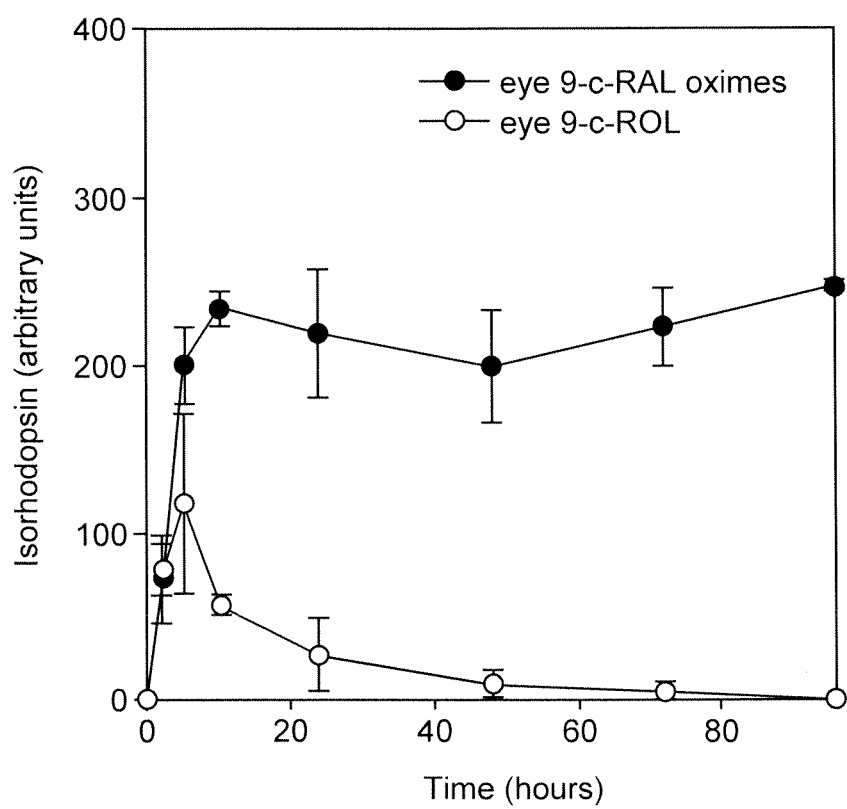
FIG. 2. Eye 9-cis-retinal oximes and 9-cis-retinol time course, 20 µM gavage.

9-cis-retinyl ester restores visual pigment in an LCA mouse model. LRAT−/− mice were gavaged with all-transretinyl palmitate, all-trans-retinyl acetate or 9-cis-retinyl acetate as indicated in the legend to FIG. 1. Following treatment, retinoids were extracted from the eye and liver, and analyzed by HPLC. As shown in FIG. 1 left, treatment of mice only with 9-cis-retinyl acetate, but not with all-trans-retinyl analogs restored the presence of syn-9-cis-retinal oxime, indicating formation of the chromophore and restoration vision in these mice. No significant retention of retinoids was observed in liver, where LRAT is highly expressed, indicating low or no toxicity by retinoids in this animal model of human LCA. 9-cis-retinyl ester restores visual pigment in approximately 5 hr (FIG. 2), while excess of retinoid is removed and metabolized (as illustrated for 9-cis-retinol).

Example 2

Vitamin A and its derivatives can isomerized upon exposure to light. For example, Rao et al. (*Tetrahedron Letters* 31:3441-44 (1990)) showed photoisomerization of all-trans-retinol acetate (a derivative of Vitamin A) using a broad wavelength UV light could produce a mixture of all-trans, 13-cis, and 9-cis retinol acetate isomers. However, this methods is generally inefficient and produces small amounts of such retinoid.

Methods

Solutions of all-trans-retinoids are made to concentrations of 1 mg/mL in methanol. The solutions are added to a glass petri dish and subjected to 365 nm UV light using a Bio-Rad GS Genelinker with the stock bulbs replaced with 8 watt F8T5 bulbs, for varying lengths of time dependent on the target retinoid. This wavelength is beneficial, as shorter wave length light quickly destroys retinoids. Following UV-treatment, the solutions are dried down, dissolved in hexane, and purified using normal phase HPLC. Conversion yields vary for each all-trans derivative. Nonisomerized all-trans derivatives, or 13-cis and 11-cis derivatives can be reused in subsequent repetitions, thereby increasing yields.

Results

Production of 9-Cis-Retinyl Acetate from all-Trans-Retinyl Acetate

Figure 3:
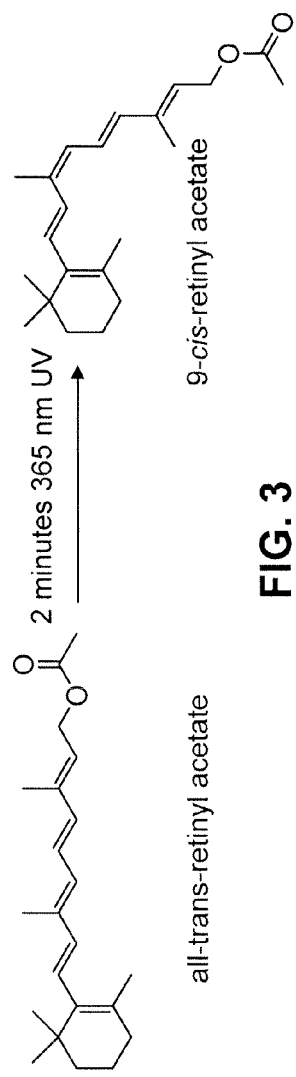
FIG. 3. UV isomerization of all-trans-retinyl acetate to 9-cis-retinyl acetate.
Figure 4:
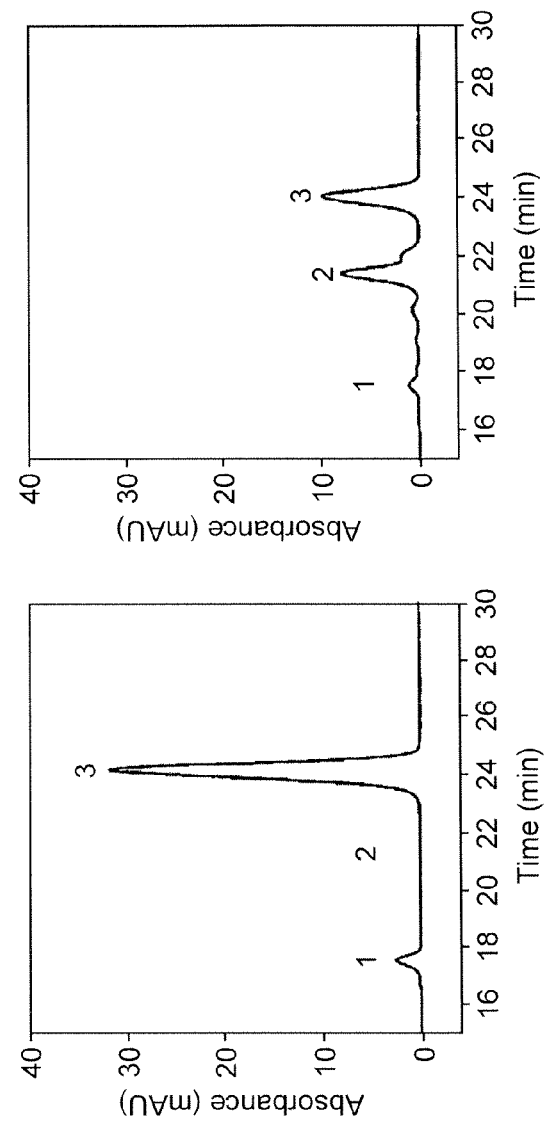
FIG. 4. HPLC separation of 13-cis-retinyl acetate (1), 9-cis-retinyl acetate (2), and all-trans-retinyl acetate (3).

All-trans-retinyl acetate (Sigma #R4632) was dissolved in methanol to a concentration of 1 mg/mL. The solution was poured into a glass petri dish and irradiated with 365 nm UV light, inducing isomerization (FIG. 3). Two minutes of irradiation yields a mix of isomers, ~25% 9-cis-retinyl acetate, as shown by HPLC (FIG. 4).

The following diagram illustrates some other compounds that can be made with this method.

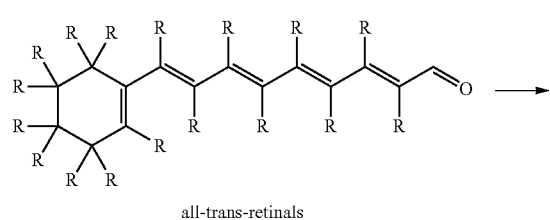
all-trans-retinals

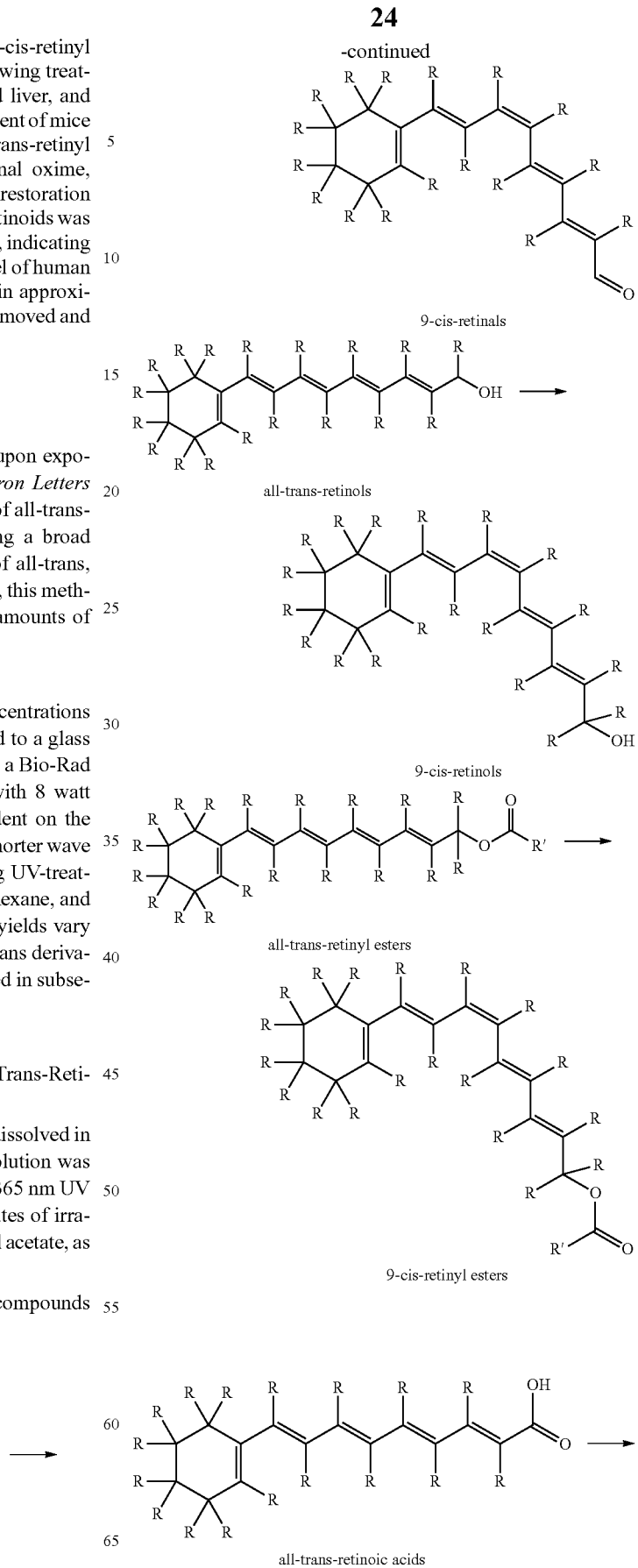

-continued

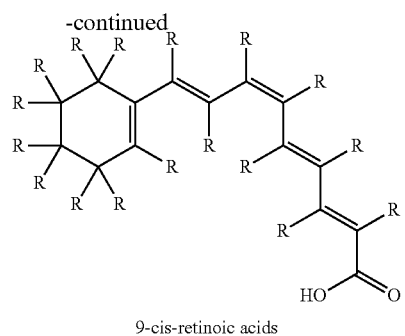

9-cis-retinoic acids

R is hydrogen or lower alkyls ranging from $C_1$ to $C_6$. R' is R or any higher alkyls such as palmitate, oleate, or complex groups such as succinate, fumarate, and other functional groups.

Example 3

Levels of 9-cis-RAL oximes (measured as syn- and anti-9-cis-retinyl aldehyde) in the eyes of Lrat−/− mice after a single dose or multiple doses of 9-cis-retinyl-acetate (9-cis-R-Ac). Doses of 9-cis-R-Ac were administered to Lrat−/− mice by oral gavage in vegetable oil (100% canola oil) in a volume of 500 µl (2.5 mg/ml). The mice weighed about 30-50 g. After 3 days, 9-cis-RAL oximes levels were determined by HPLC. Briefly, all experimental procedures related to extraction, derivatization, and separation of retinoids from dissected mouse eyes were carried out as described previously. See Van Hooser et al., J. Biol. Chem. 277:19173-182 (2002); Van Hooser et al., Proc. Natl. Acad. Sci. USA 97:8623-28 (2000); Maeda et al., J. Neurochem. 85:944-56 (2003). All reactions involving retinoids were carried out under dim red light.

Figure 5:
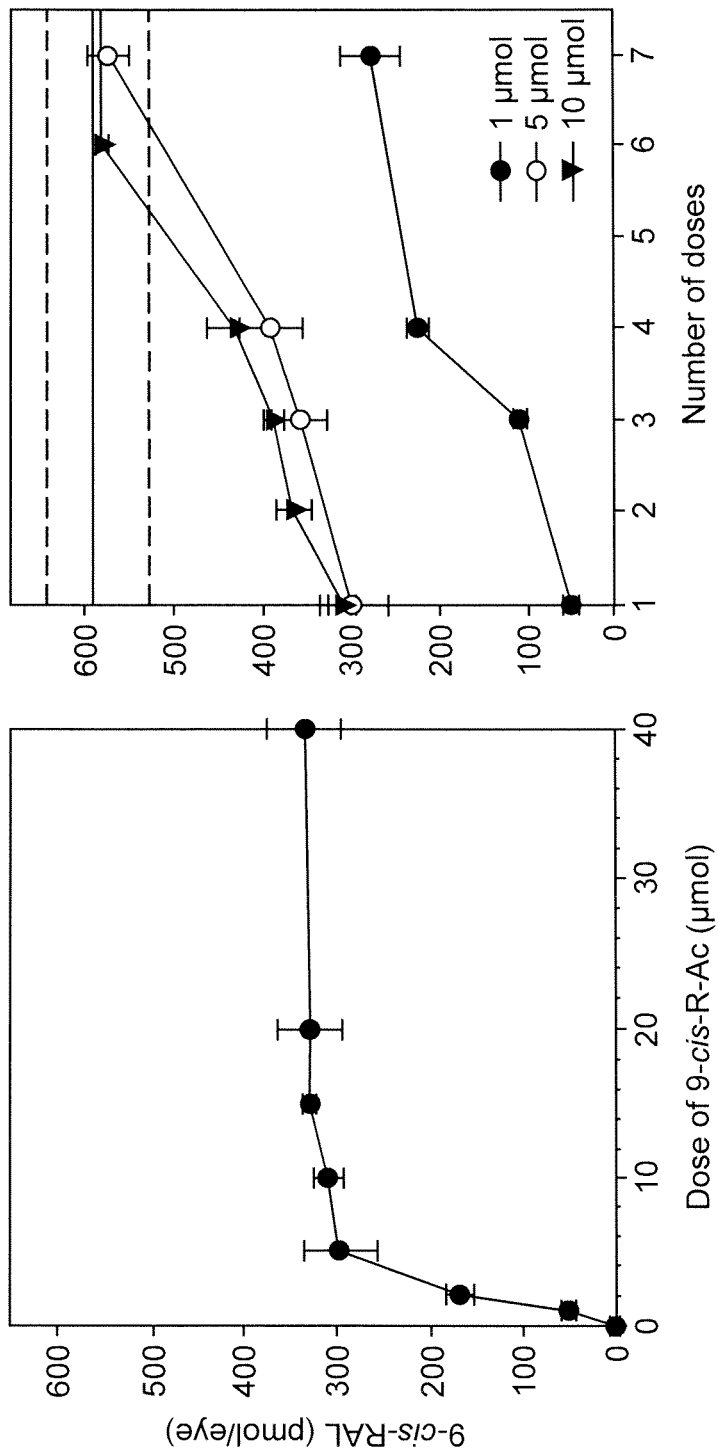
FIG. 5. Levels of 9-cis-retinal oximes in the eyes of Lrat−/− mice after a single or multiple dose of 9-cis-R-Acetate. (a) The level of 9-cis-RAL in Lrat−/− mouse eyes after a varying dose of 9-cis-R-Ac. (b) The level of 9-cis-RAL in Lrat−/− mouse eyes after a varying size and number of doses of 9-cis-R-Ac.

Referring to FIG. 5a, the level of 9-cis-RAL in Lrat−/− in mouse eyes after a varying dose of 9-cis-R-Ac is shown. Peaks were identified by retention time and UV spectra and compared to standards. The spike around 19 min resulted from changes in the solvent composition. Retinoid analysis was performed on an HP1100 HPLC equipped with a diode array detector and HP Chemstation (A.07.01) software, allowing identification of retinoid isomers according to their specific retention time and absorption maxima. A normal-phase column (Beckman Ultrasphere Si 5µ, 4.6 mm×250 mm) and an isocratic solvent system of 0.5% ethyl acetate in hexane (v/v) for 15 min, followed by 4% ethyl acetate in hexane for 60 min at a flow rate of 1.4 ml/min (total 80 min), with detection at 325 nm allowed the partial separation of 11-cis-retinyl esters, 13-cis-retinyl esters, and all-trans-retinyl esters at 20° C.

Levels of 9-cis-RAL per eye leveled off at doses of about 4-6 µmole. Referring to FIG. 5b, the level of 9-cis-RAL in Lrat−/− mouse eyes after a varying size and number of doses of 9-cis-R-Ac is shown. Levels of 9-cis-RAL accumulated over time. The levels of 9-cis-RAL increased from about 50 mmole per eye to about 600 µmole per eye. The gray solid line represents a maximal level of isorhodopsin as measured by the level of 9-cis-retinal oximes in Lrat−/− mouse eyes after 10 gavages; dashed gray lines indicate the standard deviations. The maximal level of isorhodopsin is comparable to the level of rhodopsin in wildtype (WT) mice.

Example 4

Levels of chromophore (opsin/retinal complexes) were measured in the eyes of mice after dosing with all-trans-retinoid isoforms or 9-cis-retinyl succinate. All-trans-retinyl-palmitate, all-trans-retinyl acetate, all-trans-retinal (vitamin A aldehyde), all-trans-retinol (vitamin A), all-trans-retinyl succinate and 9-cis-retinyl succinate were administered to Lrat−/− mice by oral gavage. Five milligrams of the retinoid isoforms or 9-cis-retinyl succinate were administered in 100% canola oil at a concentration of 40 mg/ml. After 3 days, chromophore levels (as all-trans-retinal oximes or 9-cis-retinal oximes) were determined as described previously. See Van Hooser et al., J. Biol. Chem. 277:19173-182 (2002); Van Hooser et al., Proc. Natl. Acad. Sci. USA 97:8623-28 (2000); Maeda et al., J. Neurochem. 85:944-56 (2003). All reactions involving retinoids were carried out under dim red light.

Figure 6:
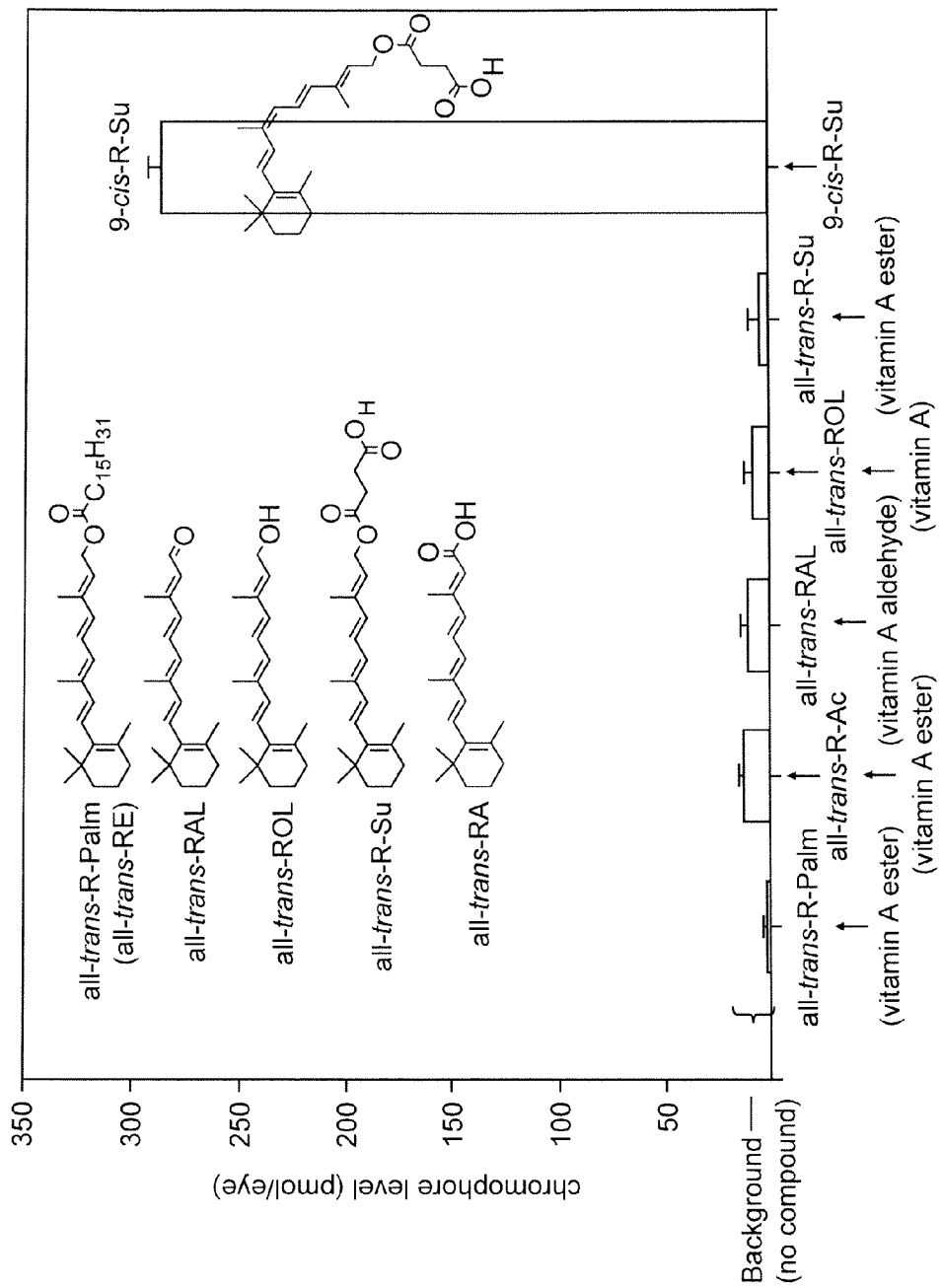
FIG. 6. Chromophore levels (as 9-cis-retinal oximes) in the eyes of Lrat−/− mice after administration of all-trans-retinoid isomers or 9-cis-retinyl succinate). The structures of the all-trans-retinoid isomers and 9-cis-retinyl succinate are also shown.

Referring to FIG. 6, the all-trans retinoid isoforms had essentially no effect on restoration of chromophore levels. In contrast, administration of 9-cis-retinyl succinate restored chromophore levels.

Example 5

A comparison of the bioavailability of orally delivered 9-cis-retinaldehyde and 9-cis-retinyl acetate in an LRAT −/− model. 9-cis-retinaldehyde and 9-cis-retinyl acetate were administered at low (10 mmoles) and high (15 mmoles) doses to LRAT−/− mice. Chromophore levels (as 9-cis-retinal oximes) were determined as described previously. See Van Hooser et al., J. Biol. Chem. 277:19173-182 (2002); Van Hooser et al., Proc. Natl. Acad. Sci. USA 97:8623-28 (2000); Maeda et al., J. Neurochem. 85:944-56 (2003). All reactions involving retinoids were carried out under dim red light.

Figure 7:
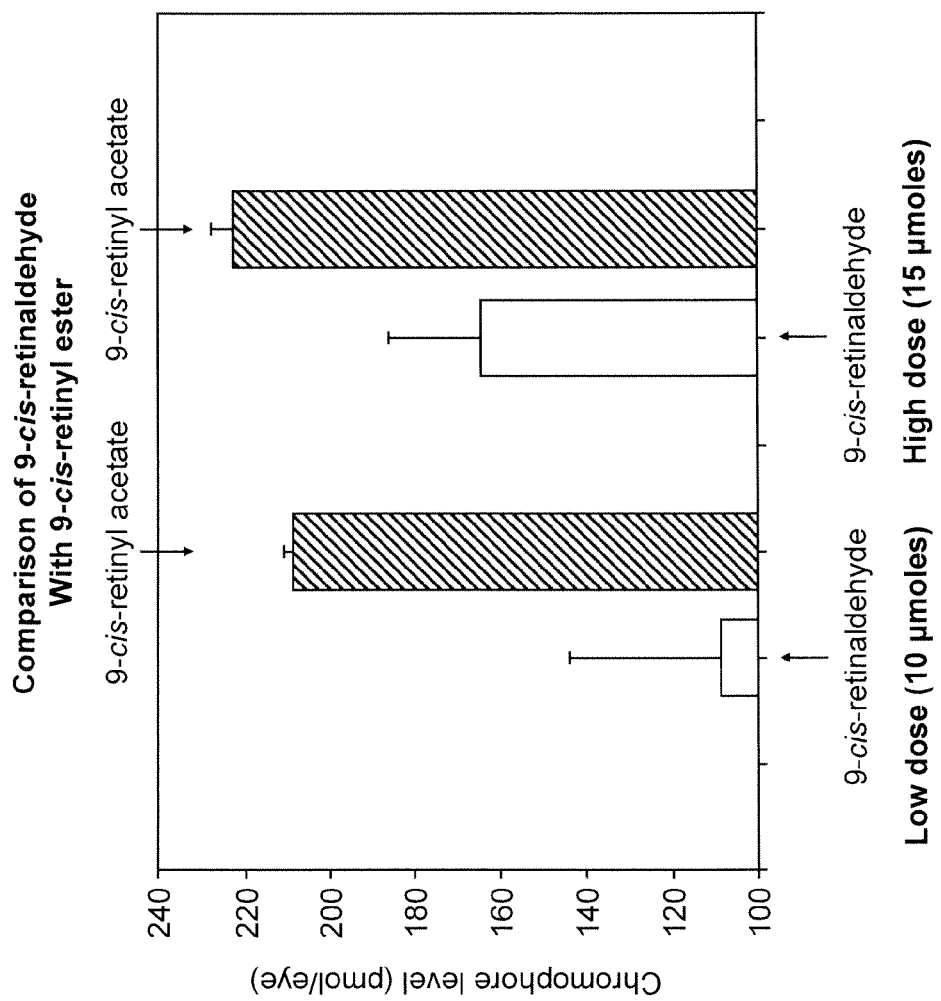
FIG. 7. A comparison of the chromophore levels (as 9-cis-retinal oximes) in the eyes of Lrat−/− mice after administration of 9-cis-retinal or 9-cis-retinyl acetate at low and high doses.

Referring to FIG. 7, at low and high doses, administration of 9-cis-retinyl acetate more efficiently restores chromophore levels than 9-cis-retinaldehyde. This effect is more pronounced at low (10 µmoles) doses. Because administration of retinoids can lead to toxicity, pro-drugs such as retinyl esters (e.g., 9-cis-retinyl acetate) provide a suitable bioavailable form to restore chromophore levels while reducing risk associated with retinoid toxicity.

The previous examples are provided to illustrate but not to limit the scope of the claimed inventions. Other variants of the inventions will be readily apparent to those of ordinary skill in the art and encompassed by the appended claims. All publications, patents, patent applications and other references cited herein are hereby incorporated by reference.

What is claimed is:

1. A retinyl ester selected from the group consisting of a 9-cis-retinyl ester of Formula I and an 11-cis-retinyl ester of Formula II, wherein A is $CH_2OR$ and —R, when taken together with the adjacent oxygen is a carboxylate radical of a $C_2$ to $C_{10}$ polycarboxylic acid:

Formula I

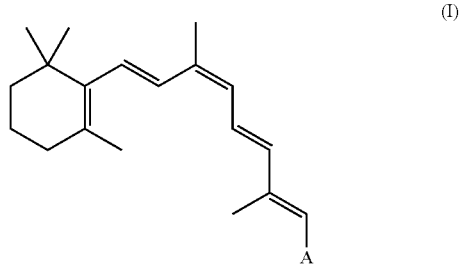

(I)

Formula II

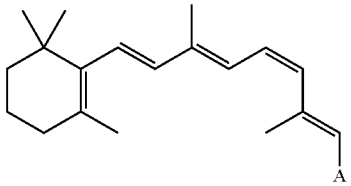

wherein the ester substituent is selected from the group consisting of oxalate, malonate, succinate, citrate, ketoglutarate, fumarate, malate, glutarate, adipate, pimelate, suberate, azelate, sebacate, and oxaloacetate;

wherein the retinyl ester is a pro-drug that, when administered to a subject, is metabolically transformed into a retinal capable of binding opsin.

2. The retinyl ester of claim 1, which is a 9-cis-retinyl ester of Formula I.

3. The retinyl ester of claim 2, wherein the 9-cis-retinyl ester is 9-cis-retinyl succinate, 9-cis-retinyl citrate, 9-cis-retinyl ketoglutarate, 9-cis-retinyl fumarate, 9-cis-retinyl malate or 9-cis-retinyl oxaloacetate.

4. The retinyl ester of claim 3, wherein the 9-cis-retinyl ester is 9-cis-retinyl succinate.

5. The retinyl ester of claim 1, which is an 11-cis-retinyl ester of Formula II.

6. The retinyl ester of claim 5, wherein the 11-cis-retinyl ester is 11-cis-retinyl succinate, 11-cis-retinyl citrate, 11-cis-retinyl ketoglutarate, 11-cis-retinyl fumarate, 11-cis-retinyl malate or 11-cis-retinyl oxaloacetate.

7. A retinyl ester selected from the group consisting of a 9-cis-retinyl ester of Formula I:

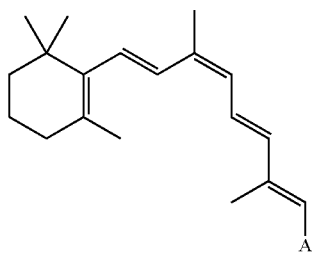

and an 11-cis-retinyl ester of Formula II:

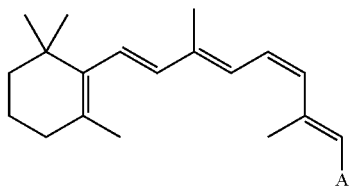

wherein A is $CH_2OR$ and R forms a retinyl ester, wherein the ester substituent comprises a carboxylate radical of a $C_3$ to $C_{10}$ polycarboxylic acid;

wherein the ester substituent is selected from the group consisting of malonate, succinate, citrate, ketoglutarate, fumarate, malate, glutarate, adipate, pimelate, suberate, azelate, sebacate, and oxaloacetate; and wherein the retinyl ester is a pro-drug that, when administered to a subject, is metabolically transformed into a retinal capable of binding opsin.

8. The retinyl ester of claim 7, which is a 9-cis-retinyl ester of Formula I.

9. The retinyl ester of claim 8, wherein the 9-cis-retinyl ester is 9-cis-retinyl succinate, 9-cis-retinyl citrate, 9-cis-retinyl ketoglutarate, 9-cis-retinyl fumarate, 9-cis-retinyl malate or 9-cis-retinyl oxaloacetate.

10. The retinyl ester of claim 9, wherein the 9-cis-retinyl ester is 9-cis-retinyl succinate.

11. The retinyl ester of claim 7, which is an 11-cis-retinyl ester of Formula II.

12. The retinyl ester of claim 11, wherein the 11-cis-retinyl ester is 11-cis-retinyl succinate, 11-cis-retinyl citrate, 11-cis-retinyl ketoglutarate, 11-cis-retinyl fumarate, 11-cis-retinyl malate or 11-cis-retinyl oxaloacetate.

\* \* \* \* \*